(12) United States Patent
Hunt et al.

(10) Patent No.: US 12,370,175 B2
(45) Date of Patent: *Jul. 29, 2025

(54) GLUCOCORTICOID RECEPTOR MODULATORS TO TREAT PANCREATIC CANCER

(71) Applicant: Corcept Therapeutics, Inc., Menlo Park, CA (US)

(72) Inventors: Hazel Hunt, Storrington (GB); Thaddeus S. Block, Menlo Park, CA (US)

(73) Assignee: Corcept Therapeutics, Inc., Redwood City, CA (US)

( * ) Notice: Subject to any disclaimer, the term of this patent is extended or adjusted under 35 U.S.C. 154(b) by 238 days.

This patent is subject to a terminal disclaimer.

(21) Appl. No.: 18/124,959

(22) Filed: Mar. 22, 2023

(65) Prior Publication Data

US 2023/0285361 A1    Sep. 14, 2023

Related U.S. Application Data

(63) Continuation of application No. 17/075,902, filed on Oct. 21, 2020, now Pat. No. 11,642,331, which is a continuation of application No. 16/843,727, filed on Apr. 8, 2020, now Pat. No. 10,828,280, which is a continuation of application No. 16/550,048, filed on Aug. 23, 2019, now Pat. No. 10,646,474, which is a continuation of application No. 16/260,360, filed on Jan. 29, 2019, now Pat. No. 10,449,178, which is a continuation of application No. 16/150,916, filed on Oct. 3, 2018, now Pat. No. 10,213,414, which is a continuation of application No. 15/915,477, filed on Mar. 8, 2018, now Pat. No. 10,117,852, which is a continuation of application No. 15/697,878, filed on Sep. 7, 2017, now Pat. No. 9,943,505.

(60) Provisional application No. 62/385,590, filed on Sep. 9, 2016.

(51) Int. Cl.

| A61K 31/416 | (2006.01) |
|---|---|
| A61K 31/03 | (2006.01) |
| A61K 31/18 | (2006.01) |
| A61K 31/337 | (2006.01) |
| A61K 31/4192 | (2006.01) |
| A61K 31/44 | (2006.01) |
| A61K 31/473 | (2006.01) |
| A61K 31/513 | (2006.01) |
| A61K 31/7068 | (2006.01) |
| A61K 33/243 | (2019.01) |
| A61K 45/06 | (2006.01) |

(52) U.S. Cl.
CPC .......... *A61K 31/416* (2013.01); *A61K 31/03* (2013.01); *A61K 31/18* (2013.01); *A61K 31/337* (2013.01); *A61K 31/4192* (2013.01); *A61K 31/44* (2013.01); *A61K 31/473* (2013.01); *A61K 31/513* (2013.01); *A61K 31/7068* (2013.01); *A61K 33/243* (2019.01); *A61K 45/06* (2013.01)

(58) Field of Classification Search
None
See application file for complete search history.

(56) References Cited

U.S. PATENT DOCUMENTS

| 7,928,237 B2 | 4/2011 | Clark et al. |
|---|---|---|
| 8,461,172 B2 | 6/2013 | Clark et al. |
| 8,658,128 B2 | 2/2014 | Altschul et al. |
| 8,710,035 B2 | 4/2014 | Pan et al. |
| 9,114,147 B2 | 8/2015 | Altschul et al. |
| 9,149,485 B2 | 10/2015 | Pan et al. |
| 9,289,436 B2 | 3/2016 | Szmulewitz et al. |
| 9,314,473 B2 | 4/2016 | Altschul et al. |

(Continued)

FOREIGN PATENT DOCUMENTS

| JP | 2013527233 A | 6/2013 |
|---|---|---|
| JP | 2019507159 A | 3/2019 |

(Continued)

OTHER PUBLICATIONS

Ali et al., "Novel N-Arylpyrazolo[3,2-c]-Based Ligands for the Glucocorticoid Receptor: Receptor Binding and in Vivo Activity", Journal of Medicinal Chemistry, vol. 47, Apr. 2, 2004, pp. 2441-2452.

(Continued)

*Primary Examiner* — Brian J Davis
(74) *Attorney, Agent, or Firm* — Kilpatrick Townsend & Stockton LLP

(57) ABSTRACT

Methods and compositions for treating a subject hosting a non-ACTH-secreting pancreatic tumor are disclosed. The methods include administering to the subject a chemotherapeutic agent and a glucocorticoid receptor modulator (GRM), preferably a selective glucocorticoid receptor modulator (SGRM), to reduce the tumor load in the subject. The non-ACTH-secreting pancreatic tumor may be an exocrine pancreatic tumor. The GRM may be a nonsteroidal GRM or a nonsteroidal SGRM. The nonsteroidal SGRM may be a nonsteroidal compound comprising: a fused azadecalin structure; a heteroaryl ketone fused azadecalin structure; or an octahydro fused azadecalin structure. Pharmaceutical compositions comprising a chemotherapeutic agent and a GRM are disclosed. The GRM in such pharmaceutical compositions may be a nonsteroidal GRM, and may be a nonsteroidal SGRM. The nonsteroidal SGRM may comprise: a fused azadecalin structure; a heteroaryl ketone fused azadecalin structure; or an octahydro fused azadecalin structure.

18 Claims, 1 Drawing Sheet

(56) References Cited

U.S. PATENT DOCUMENTS

| | | | |
|---|---|---|---|
| 9,320,747 | B1 | 4/2016 | Altschul et al. |
| 9,623,032 | B2 | 4/2017 | Pan et al. |
| 9,801,893 | B2 | 10/2017 | Szmulewitz et al. |
| 9,820,949 | B2 | 11/2017 | Desai et al. |
| 9,943,505 | B2 | 4/2018 | Hunt et al. |
| 10,117,852 | B2 | 11/2018 | Hunt et al. |
| 10,213,414 | B2 | 2/2019 | Hunt et al. |
| 10,449,178 | B2 | 10/2019 | Hunt et al. |
| 10,646,474 | B2 | 5/2020 | Hunt et al. |
| 10,828,280 | B2 | 11/2020 | Hunt et al. |
| 2007/0281928 | A1 | 12/2007 | Clark et al. |
| 2009/0129647 | A1 | 5/2009 | Dimitrova et al. |
| 2014/0038926 | A1 | 2/2014 | Hunt et al. |
| 2015/0148341 | A1 | 5/2015 | Hunt et al. |
| 2016/0215049 | A1 | 7/2016 | Feldhaus et al. |
| 2018/0071255 | A1 | 3/2018 | Hunt et al. |
| 2019/0083486 | A1 | 3/2019 | Hunt |

FOREIGN PATENT DOCUMENTS

| | | |
|---|---|---|
| WO | 2013039916 A1 | 3/2013 |
| WO | 2013177559 A2 | 11/2013 |
| WO | 2015077530 A1 | 5/2015 |
| WO | 2016055533 A1 | 4/2016 |
| WO | 2016055537 A1 | 4/2016 |
| WO | 2018049255 A1 | 3/2018 |

OTHER PUBLICATIONS

European Patent Application No. 17849673.3 , "Office Action", Aug. 23, 2023, 7 pages.
U.S. Appl. No. 15/697,878 , Non-Final Office Action, Mailed on Jan. 12, 2018, 11 pages.
U.S. Appl. No. 15/697,878 , Notice of Allowance, Mailed on Feb. 23, 2018, 9 pages.
U.S. Appl. No. 15/915,477 , Final Office Action, Mailed on Aug. 13, 2018, 9 pages.
U.S. Appl. No. 15/915,477 , Non-Final Office Action, Mailed on Jun. 12, 2018, 11 Pages.
U.S. Appl. No. 15/915,477 , Notice of Allowance, Mailed on Aug. 27, 2018, 11 pages.
U.S. Appl. No. 16/150,916 , Non-Final Office Action, Mailed on Nov. 1, 2018, 10 pages.
U.S. Appl. No. 16/150,916 , Notice of Allowance, Mailed on Jan. 11, 2019, 8 pages.
U.S. Appl. No. 16/260,360 , Non-Final Office Action, Mailed on Mar. 28, 2019, 9 pages.
U.S. Appl. No. 16/260,360 , Notice of Allowance, Mailed on Jul. 3, 2019, 8 pages.
U.S. Appl. No. 16/550,048 , Non-Final Office Action, Mailed on Oct. 4, 2019, 9 pages.
U.S. Appl. No. 16/550,048 , "Notice of Allowability", Apr. 8, 2020, 4 pages.
U.S. Appl. No. 16/550,048 , Notice of Allowance, Mailed on Jan. 15, 2020, 8 pages.
U.S. Appl. No. 16/843,727 , Non-Final Office Action, Mailed on Jun. 11, 2020, 11 pages.
U.S. Appl. No. 16/843,727 , Notice of Allowance, Mailed on Sep. 17, 2020, 8 pages.
U.S. Appl. No. 17/075,902 , Non-Final Office Action, Mailed on Dec. 1, 2022, 18 pages.
U.S. Appl. No. 17/075,902 , Notice of Allowance, Mailed on Feb. 28, 2023, 9 pages.
Benagiano et al., "Selective Progesterone Receptor Modulators 3: Use in Oncology, Endocrinology and Psychiatry", Expert Opinion. Pharmacother, vol. 9, No. 14, Oct. 2008, pp. 2487-2496.
Check et al., "Evidence that Mifepristone, A Progesterone Receptor Antagonist, Can Cross the Blood Brain Barrier and Provide Palliative Benefits for Glioblastoma Multiforme Grade IV", Anticancer Research, vol. 34, No. 5, May 2014, pp. 2385-2388.
Check et al., "Mifepristone Causing Complete Remission of Rapidly Advancing Leukemia with Measurement of Progesterone-Induced Blocking Factor", Anticancer Research, vol. 34, No. 5, May 2014, pp. 2413-2416.
Chilean Patent Application No. 201900569 , Office Action, Mailed on Aug. 10, 2020, 18 pages.
Cossu et al., "The Role of Mifepristone in Meningiomas Management: A Systematic Review of the Literature", BioMed Research International, vol. 2015, Jul. 2015, pp. 1-11.
European Patent Application No. 17849673.3 , Extended European Search Report, Mailed on Mar. 26, 2020, 11 pages.
Japanese Patent Application No. 2019-512982 , Office Action, Mailed on Jul. 1, 2020, 6 pages.
Kach et al., "Glucocorticoid Receptor Signaling in Breast and Prostate Cancers: Emergence as a Therapeutic Target", Science Translational Medicine, vol. 7, No. 305, Sep. 16, 2015, 9 pages.
Kach et al., "Selective Glucocorticoid Receptor Modulators (SGRMs) Delay Castrate-Resistant Prostate Cancer Growth", Molecular Cancer Therapeutics, vol. 16, No. 8, Aug. 2017, pp. 1680-1692.
Kondo et al., "A Case of Ectopic Adrenocorticotropic Hormone-Producing Pancreatic Neuroendocrine Tumor with Multiple Liver Metastases", Endocrine Journal, vol. 57, No. 3, Apr. 2010, pp. 229-236.
Norman et al., "Functional Glucocorticoid Receptor Modulates Pancreatic Carcinoma Growth Through an Autocrine Loop", Journal of Surgical Research, vol. 57, No. 1, Jul. 1994, pp. 33-38.
International Patent Application No. PCT/US2017/050812 , International Preliminary Report on Patentability, Mailed on Mar. 21, 2019, 12 pages.
International Patent Application No. PCT/US2017/050812 , International Search Report and Written Opinion, Mailed on Dec. 26, 2017, 17 pages.
Schlossmacher et al., "Glucocorticoid Receptor-Mediated Apoptosis: Mechanisms of Resistance in Cancer Cells", Journal of Endocrinology, vol. 211, No. 1, Oct. 2011, pp. 17-25.
Touat et al., "Successful Treatment of Multiple Intracranial Meningiomas with the Antiprogesterone Receptor Agent Mifepristone (RU486)", Acta Neurochirurgica, vol. 156, No. 10, Oct. 2014, pp. 1831-1835.
Von Hoff et al., "Increased Survival in Pancreatic Cancer with Nab-Paclitaxel Plus Gemcitabine", The New England Journal of Medicine, vol. 369, No. 18, Oct. 31, 2013, pp. 1691-1703.
Zhang et al., "Corticosteroid Co-Treatment Induces Resistance to Chemotherapy in Surgical Resections, Xenografts and Established Cell Lines of Pancreatic Cancer", BMC Cancer, vol. 6, No. 61, Mar. 15, 2006, pp. 1-14.
European Patent Application No. 17849673.3 , Office Action, Mailed on Dec. 10, 2024, 6 pages.
Kim et al., "Phase II Study of 5-Fluorouracil and Paclitaxel in Patients with Gemcitabine-Refractory Pancreatic Cancer", Cancer Chemotherapy and Pharmacology, vol. 63, No. 3, XP019655122, Sep. 3, 2008, pp. 529-533.
Matos et al., "A Pilot Study of Perillyl Alcohol in Pancreatic Cancer", Journal of Surgical Research, vol. 147, No. 2, XP022672697, Jun. 15, 2008, pp. 194-199.

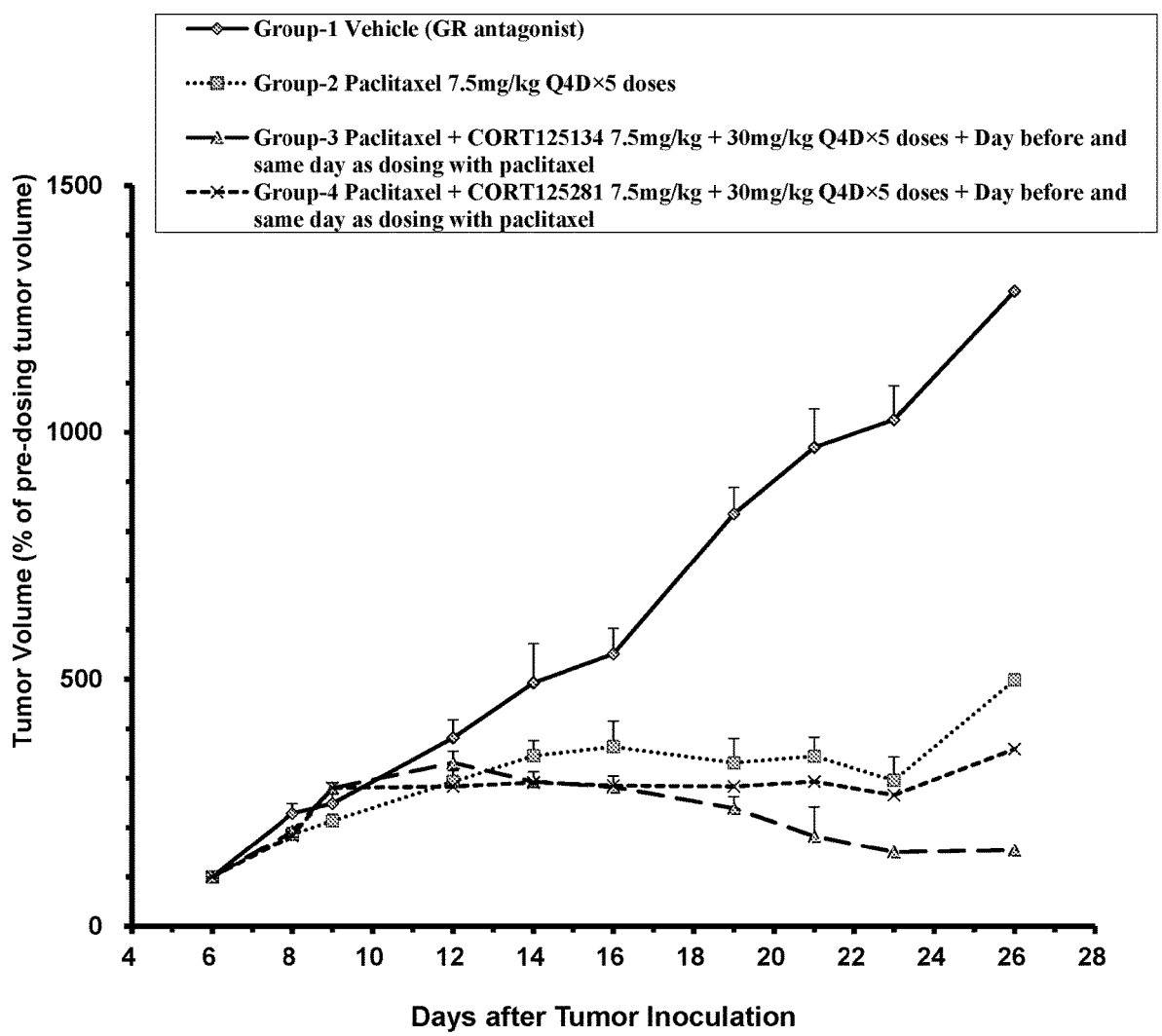

GLUCOCORTICOID RECEPTOR MODULATORS TO TREAT PANCREATIC CANCER

CROSS-REFERENCE TO RELATED APPLICATION

This application is a Continuation of U.S. patent application Ser. No. 17/075,902, filed Oct. 21, 2020, which is a Continuation of U.S. patent application Ser. No. 16/843,727, filed Apr. 8, 2020 (now U.S. Pat. No. 10,828,280, issued Nov. 10, 2020), which is a Continuation of U.S. patent application Ser. No. 16/550,048, filed Aug. 23, 2019 (now U.S. Pat. No. 10,646,474, issued May 12, 2020), which is a Continuation of U.S. patent application Ser. No. 16/260,360, filed Jan. 29, 2019 (now U.S. Pat. No. 10,449,178, issued Oct. 22, 2019), which is a Continuation of U.S. patent application Ser. No. 16/150,916, filed Oct. 3, 2018 (now U.S. Pat. No. 10,213,414, issued Feb. 26, 2019), which is a Continuation of U.S. patent application Ser. No. 15/915,477, filed Mar. 8, 2018 (now U.S. Pat. No. 10,117,852, issued Nov. 6, 2018), which is a Continuation of U.S. patent application Ser. No. 15/697,878, filed Sep. 7, 2017 (now U.S. Pat. No. 9,943,505, issued Apr. 17, 2018), which claims priority to and the benefit of U.S. Provisional Patent Application No. 62/385,590, filed Sep. 9, 2016, which applications are hereby incorporated by reference herein in their entireties.

BACKGROUND

Pancreatic cancer is the fifth leading cause of cancer death in the United States. It is more common among men, and men between the ages of 60 and 70 are most at risk. Pancreatic cancer usually begins in the ducts of the pancreas when abnormal cells within the pancreas grow out of control and form a tumor. More than 95% of pancreatic cancers are classified as exocrine pancreatic tumors. These tumors start in the exocrine cells that make pancreatic enzymes that help in digestion. Neuroendocrine pancreatic tumors account for less than 5% of all pancreatic tumors and they tend to grow slower than exocrine tumors. Pancreatic neuroendocrine tumors develop from the abnormal growth of endocrine (hormone-producing) cells in the pancreas called islet cells and thus are often referred to as "islet cell tumors." Pancreatic cancer often has a poor prognosis, even when diagnosed early, and signs and symptoms may not appear until the cancer is quite advanced and complete surgical removal is not possible.

Conventional treatment options for pancreatic cancer include surgery, radiation therapy (also termed "radiotherapy") and chemotherapy. For the reasons stated above, only 15-25% of tumors are resectable at the time of diagnosis and regrettably only 10-20% of patients resected will survive more than two years. Pancreatic tumors that are at an advanced stage often require radiotherapy or chemotherapy treatment.

Radiotherapy requires maximized exposure of the affected tissues while sparing normal surrounding tissues. Interstitial therapy, where needles containing a radioactive source are embedded in the tumor, has become a valuable new approach. In this way, large doses of radiation can be delivered locally while sparing the surrounding normal structures. Intraoperative radiotherapy, where the beam is placed directly onto the tumor during surgery while normal structures are moved safely away from the beam, is another specialized radiation technique. Again, this achieves effective irradiation of the tumor while limiting exposure to surrounding structures. Despite the obvious advantage of approaches predicated upon local control of the irradiation, patient survival rate is still very low.

Chemotherapy relies upon a generalized damage to DNA and destabilization of chromosomal structure which eventually leads to destruction of cancer cells. The non-selective nature of these treatments, however, often results in severe and debilitating side effects. The systemic use of these drugs may result in damage to normally healthy organs and tissues, and compromise the long-term health of the patient.

The effects of glucocorticoid receptor ("GR") mediated signaling pathway on cancer cells in general are controversial. On one hand, it is believed that activating the GR signaling pathways advantageously induces apoptosis in malignant lymphoid cancers (see Schlossmacher, J. Endocrinol. (2011) 211(1):17-25). On the other hand, it has been reported that agents blocking the GR signaling pathway can potentiate chemotherapy in killing breast cancer cells (see U.S. Pat. No. 9,149,485). It has been suggested that the combination of neoplasia-treating agents and certain GR antagonists may be used for treating over 30 types of neoplasia (cancer), including pancreatic cancer (Altschul et al., U.S. Pat. No. 8,658,128). It has also been suggested that GR inhibitors can be used in combination with a somatostatin receptor-binding agent to treat an adrenocorticotropin ("ACTH")-secreting, islet cell tumor of the pancreas (see WO 2013/039916, Niemann et al., "Compositions for and Methods of Treatment and Enhanced Detection of Non-Pituitary Tumors"). In terms of the effect on pancreatic cancer, however, the prevailing view is that glucocorticoid, e.g., dexamethasone, can relieve side effects of the chemotherapeutic agent and should be co-administered with chemotherapeutic agents in treating pancreatic cancer (see Zhang et al., BMC Cancer, 2006 Mar. 15 6: 61). Further, it has been reported that dexamethasone inhibits pancreatic cancer cell growth. See, Norman et al., J. Surg. Res. 1994 July; 57(1): 33-8. The present application, in contrast to the prevailing view that activation of GR signaling benefits pancreatic cancer patients, provides a novel and surprising combination therapy that employs compounds that inhibit GR signaling to treat patients suffering from certain types of pancreatic cancer.

BRIEF SUMMARY

Disclosed herein are novel methods for treating a subject hosting a non-ACTH-secreting pancreatic tumor. The methods comprise administering to the subject an effective amount of a chemotherapeutic agent and an effective amount of a GRM (where GRM is an acronym for "glucocorticoid receptor modulator") to reduce the tumor load of the non-ACTH-secreting pancreatic tumor in the subject. In preferred embodiments, the GRM is a nonsteroidal GRM. The methods also comprise administering to the subject an effective amount of a chemotherapeutic agent and an effective amount of a SGRM (where SGRM is an acronym for "selective glucocorticoid receptor modulator") to reduce the tumor load of the non-ACTH-secreting pancreatic tumor in the subject. In preferred embodiments, the SGRM is a nonsteroidal SGRM. In some cases, the non-ACTH-secreting pancreatic tumor is an exocrine pancreatic tumor.

In some cases, the chemotherapeutic agent is selected from the group consisting of antimicrotubule agents, alkylating agents, topoisomerase inhibitors, endoplasmic reticulum stress inducing agents, antimetabolites, mitotic inhibitors and combinations thereof. In some cases, the chemotherapeutic agent is a taxane. In some cases, the chemotherapeutic agent is selected from the group consisting of nab-paclitaxel, 5-fluorouracil (5-FU), gemcitabine, cisplatin and capecitabine.

In some cases, the GRM (e.g., a SGRM, such as a nonsteroidal SGRM) is orally administered. In some cases, the GRM is administered by transdermal application, by a nebulized suspension, or by an aerosol spray.

In some cases, the effective amount of the GRM (e.g., a SGRM, such as a nonsteroidal SGRM) is a daily dose of between 1 and 100 mg/kg/day, wherein the GRM is administered with at least one chemotherapeutic agent. In some embodiments, the daily dose of the GRM is 1, 2, 4, 6, 8, 10, 12, 14, 16, 18, 20, 30, 40, 50 60, 70, 80, 90 or 100 mg/kg/day. In some cases, the GRM is administrated for at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or 80 weeks.

In some cases, the GRM (e.g., a SGRM) is a nonsteroidal compound comprising a fused azadecalin structure. In some cases, the fused azadecalin compound is a compound having the following formula:

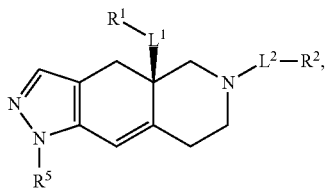

wherein $L^1$ and $L^2$ are members independently selected from a bond and unsubstituted alkylene; $R^1$ is a member selected from unsubstituted alkyl, unsubstituted heteroalkyl, unsubstituted heterocycloalkyl, —$OR^{1A}$, $NR^{1C}R^{1D}$, —$C(O)NR^{1C}R^{1D}$ and —$C(O)OR^{1A}$, wherein $R^{1A}$ is a member selected from hydrogen, unsubstituted alkyl and unsubstituted heteroalkyl, $R^{1C}$ and $R^{1D}$ are members independently selected from unsubstituted alkyl and unsubstituted heteroalkyl, wherein $R^{1C}$ and $R^{1D}$ are optionally joined to form an unsubstituted ring with the nitrogen to which they are attached, wherein said ring optionally comprises an additional ring nitrogen; $R^2$ has the formula:

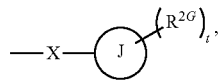

wherein $R^{2G}$ is a member selected from hydrogen, halogen, unsubstituted alkyl, unsubstituted heteroalkyl, unsubstituted cycloalkyl, unsubstituted heterocycloalkyl, —CN, and —$CF_3$; J is phenyl; t is an integer from 0 to 5; X is —$S(O_2)$—; and $R^5$ is phenyl optionally substituted with 1-5 $R^{5A}$ groups, wherein $R^{5A}$ is a member selected from hydrogen, halogen, —$OR^{5A1}$, $S(O_2)NR^{5A2}R^{5A3}$, —CN, and unsubstituted alkyl, wherein $R^{5A1}$ is a member selected from hydrogen and unsubstituted alkyl, and $R^{5A2}$ and $R^{5A3}$ are members independently selected from hydrogen and unsubstituted alkyl, or salts and isomers thereof.

In some cases, the fused azadecalin compound is

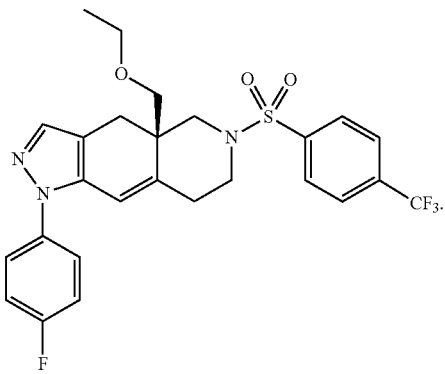 [SMILES: CCOC[C@]12Cc3cnn(-c4ccc(F)cc4)c3C=C1CCN(S(=O)(=O)c1ccc(C(F)(F)F)cc1)C2]

In some cases, the GRM (e.g., a SGRM) is a nonsteroidal compound comprising a heteroaryl ketone fused azadecalin structure or an octahydro fused azadecalin structure. In some cases, the heteroaryl ketone fused azadecalin compound has the formula:

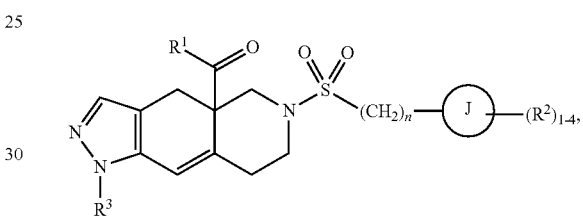

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$; each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, CN, N-oxide, $C_{3-8}$ cycloalkyl, and $C_{3-8}$ heterocycloalkyl; ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S; each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups; alternatively, two $R^2$ groups linked to the same carbon are combined to form an oxo group (=O); alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups; $R^{2a}$ and $R^{2b}$ are each independently selected from the group consisting of hydrogen and $C_{1-6}$ alkyl; each $R^{2c}$ is independently selected from the group consisting of hydrogen, halogen, hydroxy, $C_{1-6}$ alkoxy, $C_{1-6}$ haloalkoxy, CN, and $NR^{2a}R^{2b}$; each $R^{2d}$ is independently selected from the group consisting of hydrogen and $C_{1-6}$ alkyl, or two $R^{2d}$ groups attached to the same ring atom are combined to form (=O); $R^3$ is selected from the group consisting of phenyl and pyridyl, each optionally substituted with 1-4 $R^{3a}$ groups; each $R^{3a}$ is independently selected from the group consisting of hydrogen, halogen, and $C_{1-6}$ haloalkyl; and subscript n is an integer from 0 to 3; or salts and isomers thereof.

In some cases, the heteroaryl-ketone fused azadecalin compound has the formula:

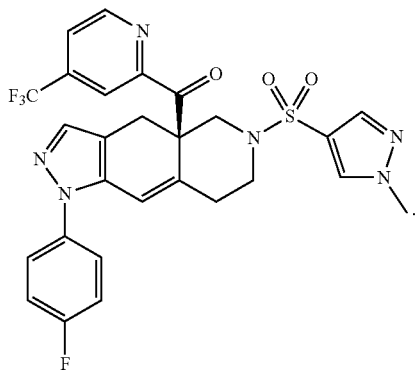 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

In some cases, the octahydro fused azadecalin compound has the formula:

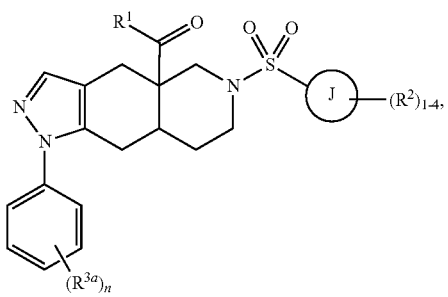

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$; each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl; ring J is selected from the group consisting of an aryl ring and a heteroaryl ring having from 5 to 6 ring members and from 1 to 4 heteroatoms each independently selected from the group consisting of N, O and S; each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl having from 1 to 3 heteroatoms each independently selected from the group consisting of N, O and S; alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups; $R^{2a}$, $R^{2b}$ and $R^{2c}$ are each independently selected from the group consisting of hydrogen and $C_{1-6}$ alkyl; each $R^{3a}$ is independently halogen; and subscript n is an integer from 0 to 3, or salts and isomers thereof.

In some cases, the nonsteroidal SGRM is CORT125134, i.e., (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, which has the following structure:

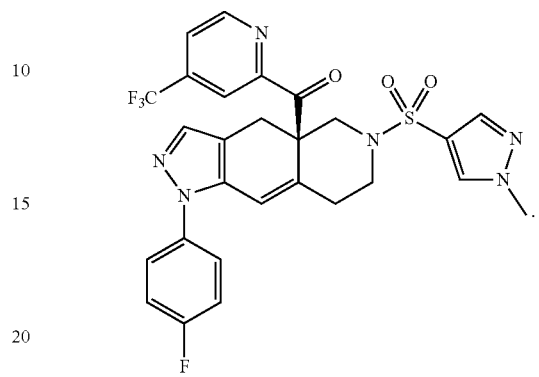

In some cases, the nonsteroidal SGRM is CORT125281, i.e., ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone, which has the following structure:

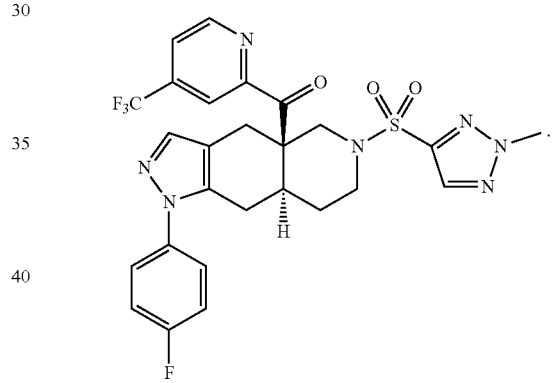

BRIEF DESCRIPTION OF THE DRAWING

The FIGURE shows tumor growth data from four (4) groups of mice that were treated with 1) vehicle, 2) paclitaxel at 7.5 mg/kg) (every four days, "Q4D"), 3) CORT125134 (30 mg/kg, dosed on day prior and same day as paclitaxel) and paclitaxel (7.5 mg/kg, Q4D), or 4) CORT125281 (30 mg/kg dosed on day prior to and same day as paclitaxel) and paclitaxel (7.5 mg/kg) (Q4D).

DETAILED DESCRIPTION

A. Introduction

The methods disclosed herein can be used to treat a patient hosting a non-ACTH-secreting pancreatic tumor by administering an effective amount of a glucocorticoid receptor modulator (GRM), preferably a selective glucocorticoid receptor modulator (SGRM), in combination with an effective amount of chemotherapy to reduce the tumor load of the pancreatic cancer. In preferred embodiments, the SGRM is a nonsteroidal SGRM. In embodiments, the nonsteroidal SGRM is a compound comprising a fused azadecalin structure. In embodiments, the nonsteroidal SGRM is a compound comprising a heteroaryl ketone fused azadecalin structure, or an octahydro fused azadecalin structure. In view of the literature reports that a GC, in combination with other agents, is the conventional treatment option for pancreatic cancer, using a SGRM in combination with a chemotherapeutic agent to reduce tumor load is surprising.

B. Definitions

As used herein, the term "tumor" and the term "cancer" are used interchangeably and both refer to an abnormal growth of tissue that results from excessive cell division. A tumor that invades the surrounding tissue and/or can metastasize is referred to as "malignant." A tumor that does not metastasize is referred to as "benign."

As used herein, the term "subject" or "patient" refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have an existing diagnosis of a pancreatic cancer which is being targeted by the compositions and methods of the present invention. In some cases, a subject may suffer from one or more types of cancer simultaneously, at least one of which is a pancreatic cancer, which is targeted by the compositions and methods of the present invention.

As used herein, the term "Adrenocorticotrophic Hormone" (ACTH) refers to the peptide hormone produced by the anterior pituitary gland that stimulates the adrenal cortex to secrete glucocorticoid hormones, which help cells synthesize glucose, catabolize proteins, mobilize free fatty acids and inhibit inflammation in allergic responses. One such glucocorticoid hormone is cortisol, which regulates metabolism of carbohydrate, fat, and protein metabolism.

As used herein, the term "non-ACTH-secreting pancreatic tumor" refers to a pancreatic tumor that is not an ACTH-secreting tumor. A "non-ACTH-secreting pancreatic tumor" does not secrete ACTH, or does not secrete more than trace amounts of ACTH, and so does not cause increased production and release of corticosteroids and cortisol from the adrenal cortex. An ACTH-secreting tumor is a non-pituitary tumor that secretes ACTH thereby causing increased production and release of corticosteroids and cortisol from the adrenal cortex. Exocrine pancreatic tumors, which counts for 95% of pancreatic tumors are believed to be non-ACTH-secreting pancreatic tumors. See, http://www.pancreaticcancer.org.uk/types. Some endocrine pancreatic tumors (also called neuroendocrine tumors), e.g., an islet cell tumor of the pancreas, are ACTH secreting tumors. See Chertman et al., Word Journal of Medical and Surgical case reports Vol. (5), available at www.npplweb.com/wjmscr/fulltext/2/13. Methods for determining whether a tumor is a ACTH-secreting tumor are well known, including but are not limited to those provided in this disclosure.

As used herein, the term "tumor load" or "tumor burden" generally refers to the number of cancer cells, the size of a tumor, or the amount of cancer in the body in a subject at any given time. Tumor load can be detected by e.g., measuring the expression of tumor specific genetic markers and measuring tumor size by a number of well-known, biochemical or imaging methods disclosed herein, infra.

As used herein, the term "effective amount" or "therapeutic amount" refers to an amount of a pharmacological agent effective to treat, eliminate, or mitigate at least one symptom of the disease being treated. In some cases, "therapeutically effective amount" or "effective amount" can refer to an amount of a functional agent or of a pharmaceutical composition useful for exhibiting a detectable therapeutic or inhibitory effect. The effect can be detected by any assay method known in the art. The effective amount can be an amount effective to invoke an antitumor response. For the purpose of this disclosure, the effective amount of SGRM or the effective amount of a chemotherapeutic agent is an amount that would reduce tumor load or bring about other desired beneficial clinical outcomes related to cancer improvement when combined with a chemotherapeutic agent or SGRM, respectively.

As used herein, the terms "administer," "administering," "administered" or "administration" refer to providing a compound or a composition (e.g., one described herein), to a subject or patient.

As used herein, the term "combination therapy" refers to the administration of at least two pharmaceutical agents to a subject to treat a disease. The two agents may be administered simultaneously, or sequentially in any order during the entire or portions of the treatment period. The at least two agents may be administered following the same or different dosing regimens. In some cases, one agent is administered following a scheduled regimen while the other agent is administered intermittently. In some cases, both agents are administered intermittently. In some embodiments, the one pharmaceutical agent, e.g., a SGRM, is administered daily, and the other pharmaceutical agent, e.g., a chemotherapeutic agent, is administered every two, three, or four days.

As used herein, the term "compound" is used to denote a molecular moiety of unique, identifiable chemical structure. A molecular moiety ("compound") may exist in a free species form, in which it is not associated with other molecules. A compound may also exist as part of a larger aggregate, in which it is associated with other molecule(s), but nevertheless retains its chemical identity. A solvate, in which the molecular moiety of defined chemical structure ("compound") is associated with a molecule(s) of a solvent, is an example of such an associated form. A hydrate is a solvate in which the associated solvent is water. The recitation of a "compound" refers to the molecular moiety itself (of the recited structure), regardless of whether it exists in a free form or an associated form.

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "glucocorticosteroid" ("GC") or "glucocorticoid" refers to a steroid hormone that binds to a glucocorticoid receptor. Glucocorticosteroids are typically characterized by having 21 carbon atoms, an $\alpha,\beta$-unsaturated ketone in ring A, and an $\alpha$-ketol group attached to ring D. They differ in the extent of oxygenation or hydroxylation at C-11, C-17, and C-19; see Rawn, "Biosynthesis and Transport of Membrane Lipids and Formation of Cholesterol Derivatives," in Biochemistry, Daisy et al. (eds.), 1989, pg. 567.

A mineralocorticoid receptor (MR), also known as a type I glucocorticoid receptor (GR I), is activated by aldosterone in humans.

As used herein, the term "Glucocorticoid receptor" ("GR") refers to a family of intracellular receptors which specifically bind to cortisol and/or cortisol analogs. The glucocorticoid receptor is also referred to as the cortisol receptor. The term includes isoforms of GR, recombinant GR and mutated GR. "Glucocorticoid receptor" ("GR") refers to the type II GR which specifically binds to cortisol and/or cortisol analogs such as dexamethasone (See, e.g., Turner & Muller, J. Mol. Endocrinol. Oct. 1, 2005 35 283-292).

"Glucocorticoid receptor modulator" (GRM) refers to any compound which inhibits any biological response associated with the binding of GR to an agonist. For example, a GR agonist, such as dexamethasone, increases the activity of tyrosine aminotransferase (TAT) in HepG2 cells (a human liver hepatocellular carcinoma cell line; ECACC, UK). Accordingly, GR modulators of the present invention can be identified by measuring the ability of the compound to inhibit the effect of dexamethasone. TAT activity can be measured as outlined in the literature by A. Ali et al., J. Med. Chem., 2004, 47, 2441-2452. A modulator is a compound with an $IC_{50}$ (half maximal inhibition concentration) of less than 10 micromolar. See Example 1, infra.

As used herein, the term "selective glucocorticoid receptor modulator" (SGRM) refers to any composition or compound which inhibits any biological response associated with the binding of a GR to an agonist. By "selective," the drug preferentially binds to the GR rather than other nuclear receptors, such as the progesterone receptor (PR), the mineralocorticoid receptor (MR) or the androgen receptor (AR). It is preferred that the selective glucocorticoid receptor modulator bind GR with an affinity that is 10× greater ($1/10^{th}$ the $K_d$ value) than its affinity to the MR, AR, or PR, both the MR and PR, both the MR and AR, both the AR and PR, or to the MR, AR, and PR. In a more preferred embodiment, the selective glucocorticoid receptor modulator binds GR with an affinity that is 100× greater ($1/100^{th}$ the $K_d$ value) than its affinity to the MR, AR, or PR, both the MR and PR, both the MR and AR, both the AR and PR, or to the MR, AR, and PR. In another embodiment, the selective glucocorticoid receptor modulator binds GR with an affinity that is 1000× greater ($1/1000^{th}$ the $K_d$ value) than its affinity to the MR, AR, or PR, both the MR and PR, both the MR and AR, both the AR and PR, or to the MR, AR, and PR.

As used herein, the terms "selective glucocorticoid receptor modulator" and "SGRM" do not include ORG 34517, or 11-(substituted phenyl)-estra-4,9-diene derivatives, or 11-(substituted phenyl)-estra-4,9-diene derivatives of the following formula:

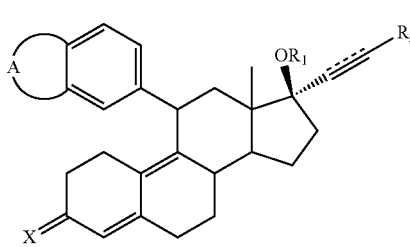

(I)

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H, OH), O, and NOH; and the interrupted line represents an optional bond (see, e.g., claim 1 of U.S. Pat. No. 8,658,128).

As used herein, the term "composition" is intended to encompass a product comprising the specified ingredients such as the said compounds, their tautomeric forms, their derivatives, their analogues, their stereoisomers, their polymorphs, their deuterated species, their pharmaceutically acceptable salts, esters, ethers, metabolites, mixtures of isomers, their pharmaceutically acceptable solvates and pharmaceutically acceptable compositions in specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, in combination, complexation or aggregation of any two or more of the ingredients, or from dissociation of one or more of the ingredients, or from other types of reactions or interactions of one or more of the ingredients. Accordingly, the pharmaceutical compositions of the present invention are meant to encompass any composition made by admixing compounds of the present invention and their pharmaceutically acceptable carriers.

In some embodiments, the term "consisting essentially of" refers to a composition in a formulation whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" can refer to compositions which contain the active ingredient and components which facilitate the release of the active ingredient. For example, the composition can contain one or more components that provide extended release of the active ingredient over time to the subject. In some embodiments, the term "consisting" refers to a composition, which contains the active ingredient and a pharmaceutically acceptable carrier or excipient.

As used herein, the phrase "nonsteroidal backbone" in the context of SGRMs refers to SGRMs that do not share structural homology to, or are not modifications of, cortisol with its steroid backbone containing seventeen carbon atoms, bonded in four fused rings. Such compounds include synthetic mimetics and analogs of proteins, including partially peptidic, pseudopeptidic and non-peptidic molecular entities.

Nonsteroidal SGRM compounds include SGRMs comprising a fused azadecalin structure (which may also be termed a fused azadecalin backbone), SGRMs comprising a heteroaryl ketone fused azadecalin structure (which may also be termed a heteroaryl ketone fused azadecalin backbone), and SGRMs comprising an octahydro fused azadecalin structure (which may also be termed an octahydro fused azadecalin backbone). Exemplary nonsteroidal glucocorticoid receptor modulators comprising a fused azadecalin structure include those described in U.S. Pat. Nos. 7,928,237 and 8,461,172. Exemplary nonsteroidal glucocorticoid receptor modulators comprising a heteroaryl ketone fused azadecalin structure include those described in U.S. 2014/0038926. Exemplary nonsteroidal glucocorticoid receptor modulators comprising an octahydro fused azadecalin structure include those described in U.S. Provisional Patent Appl. No. 61/908,333, entitled Octahydro Fused Azadecalin Glucocorticoid Receptor Modulators, filed on Nov. 25, 2013, and in U.S. patent application Ser. No. 14/549,885, filed Nov. 21, 2014.

Where substituent groups are specified by their conventional chemical formulae, written from left to right, they equally encompass the chemically identical substituents that would result from writing the structure from right to left, e.g., —$CH_2O$— is equivalent to —$OCH_2$—.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-5}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, and hexyl.

"Alkoxy" refers to an alkyl group having an oxygen atom that connects the alkyl group to the point of attachment: alkyl-O—. As for the alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Halogen" refers to fluorine, chlorine, bromine, and iodine.

"Haloalkyl" refers to alkyl, as defined above, where some or all of the hydrogen atoms are replaced with halogen atoms. As for the alkyl group, haloalkyl groups can have any suitable number of carbon atoms, such as $C_{1-6}$, and include trifluoromethyl, fluoromethyl, etc.

The term "perfluoro" can be used to define a compound or radical where all the hydrogens are replaced with fluorine. For example, perfluoromethane includes 1,1,1-trifluoromethyl.

"Haloalkoxy" refers to an alkoxy group where some or all of the hydrogen atoms are substituted with halogen atoms. As for the alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, and perfluoroethoxy.

"Cycloalkyl" refers to a saturated or partially unsaturated, monocyclic, fused bicyclic, or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene, and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1.3- and 1.4-isomers), cycloheptene, cycloheptadiene, cyclooctene, cyclooctadiene (1.3-, 1.4- and 1.5-isomers), norbornene, and norbornadiene.

When cycloalkyl is a saturated monocyclic $C_{3-8}$ cycloalkyl, exemplary groups include, but are not limited to, cyclopropyl, cyclobutyl, cyclopentyl, cyclohexyl, cycloheptyl, and cyclooctyl. When cycloalkyl is a saturated monocyclic $C_{3-6}$ cycloalkyl, exemplary groups include, but are not limited to, cyclopropyl, cyclobutyl, cyclopentyl, and cyclohexyl.

"Heterocycloalkyl" refers to a saturated ring system having from 3 to 12 ring members and from 1 to 4 heteroatoms of N, O, and S. Additional heteroatoms can also be useful, including but not limited to, B, Al, Si, and P. The heteroatoms can also be oxidized, such as, but not limited to, —S(O)— and —$S(O)_2$—. Heterocycloalkyl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1.2-, 1.3- and 1.4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as 6, 7, 8, 9, 10, 11, 12, 13, 14, 15, or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, that has a methylene linking group. Some aryl groups have from 6 to 12 ring members, such as phenyl, naphthyl, or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic, fused bicyclic, or tricyclic aromatic ring assembly containing 5 to 16 ring atoms, where from 1 to 5 of the ring atoms are a heteroatom such as N, O, or S. Additional heteroatoms can also be useful, including but not limited to, B, Al, Si, and P. The heteroatoms can also be oxidized, such as, but not limited to, N-oxide, —S(O)—, and —$S(O)_2$—. Heteroaryl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5; or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4-, and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2-, and 3-pyrrole; pyridine includes 2-, 3- and 4-pyridine; imidazole includes 1-, 2-, 4- and 5-imidazole; pyrazole includes 1-, 3-, 4- and 5-pyrazole; triazole includes 1-, 4- and 5-triazole; tetrazole includes 1- and 5-tetrazole; pyrimidine includes 2-, 4-, 5- and 6-pyrimidine; pyridazine includes 3- and 4-pyridazine; 1,2,3-triazine includes 4- and 5-triazine; 1,2,4-triazine includes 3-, 5- and 6-triazine; 1,3,5-triazine includes 2-triazine; thiophene includes 2- and 3-thiophene; furan includes 2- and 3-furan; thiazole includes 2-, 4- and 5-thiazole; isothiazole includes 3-, 4- and 5-isothiazole; oxazole includes 2-, 4- and 5-oxazole; isoxazole includes 3-, 4- and 5-isoxazole; indole includes 1-, 2- and 3-indole; isoindole includes 1- and 2-isoindole; quinoline includes 2-, 3- and 4-quinoline; isoquinoline includes 1-, 3- and 4-isoquinoline; quinazoline includes 2- and 4-quinazoline; cinnoline includes 3- and 4-cinnoline; benzothiophene includes 2- and 3-benzothiophene; and benzofuran includes 2- and 3-benzofuran.

Some heteroaryl groups include those having from 5 to 10 ring members and from 1 to 3 ring atoms including N, O, or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroatoms" refers to O, S, or N.

"Salt" refers to acid or base salts of the compounds used in the methods of the present invention. Illustrative examples of pharmaceutically-acceptable salts are mineral acid (hydrochloric acid, hydrobromic acid, phosphoric acid, and the like) salts, organic acid (acetic acid, propionic acid, glutamic acid, citric acid, and the like) salts, and quaternary ammonium (methyl iodide, ethyl iodide, and the like) salts. It is understood that the pharmaceutically-acceptable salts are non-toxic. Additional information on suitable pharmaceutically-acceptable salts can be found in Remington's Pharmaceutical Sciences, 17th ed., Mack Publishing Company, Easton, Pa., 1985, which is incorporated herein by reference.

"Isomers" refers to compounds with the same chemical formula but which are structurally distinguishable.

"Tautomer" refers to one of two or more structural isomers which exist in equilibrium and which are readily converted from one form to another.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to produce compounds which are not inherently unstable—and/or would be known to one of ordinary skill in the art as likely to be unstable under ambient conditions—such as aqueous, neutral, or physiological conditions.

"Pharmaceutically-acceptable excipient" and "pharmaceutically-acceptable carrier" refer to a substance that aids the administration of an active agent to—and absorption by—a subject and can be included in the compositions of the present invention without causing a significant adverse toxicological effect on the patient. Non-limiting examples of pharmaceutically-acceptable excipients include water, NaCl, normal saline solutions, lactated Ringer's, normal sucrose, normal glucose, binders, fillers, disintegrants, lubricants, coatings, sweeteners, flavors and colors, and the like. One of ordinary skill in the art will recognize that other pharmaceutical excipients are useful in the present invention.

C. Pancreatic Tumors

Pancreatic cancer is a malignant tumor within the pancreatic gland. Almost 90% of pancreatic cancer patients are older than 55. The average age at the time this cancer is found is 72. Risk factors for pancreatic cancer include: age, male sex, African ethnicity, smoking, diets high in meat, obesity, diabetes, chronic pancreatitis (has been linked, but is not known to be causal), occupational exposure to certain pesticides, dyes, and chemicals related to gasoline, family history, *Helicobacter pylori* infection, gingivitis or periodontal disease. (Pancreatic Cancer. Von Hoff et al., ed., Maine; 2005). Certain inherited genetic syndromes cause as many as 10% of pancreatic cancers. Genetic markers that are associated with pancreatic cancer include, e.g., mutations in the PNCA1, PALLD or BRCA2 gene (see, e.g., Banke et al., 2000, Med. Clin. North Am. 84: 677-690; Meckler et al., 2001, Am. J. Surg. Path. 25: 1047-1053; Pogue-Geile et al., 2006, PLoS Med. 3: e516; Murphy et al., 2002, Cancer Res. 62: 3789-3793). However, not all patients in the currently recognized risk categories will develop pancreatic cancers. Many pancreatic cancers arise "sporadically" (i.e., in patients without family histories).

Early pancreatic cancer symptoms are non-specific and varied. Common symptoms include pain in the upper abdomen that typically radiates to the back and is relieved by leaning forward (seen in carcinoma of the body or tail of the pancreas), loss of appetite, nausea, vomiting significant weight loss and painless jaundice related to bile duct obstruction (carcinoma of the head of the pancreas). However, all of these symptoms can have multiple other causes and are not limited to pancreatic cancer.

One or more of imaging based methods, such as, magnetic resonance imaging (MRI), computed tomography (CT), X-ray, and positron emission tomography (PET) scan, or ultrasonography (US), are often performed on subjects suspected of having pancreatic cancer, e.g., based on exhibition of the related clinical symptoms. Results from these imaging tests are often combined with the patient's medical history, physical examination and lab tests to provide accurate diagnosis as well as information regarding the origin of the tumor.

The presence of pancreatic cancer, the type and stage of pancreatic cancer can be confirmed by histological analysis of the tumor performed by a pathologist. Histology dictates many aspects of pancreatic cancer clinical treatment, management, and prognosis.

There are two main types of pancreatic cancer based on whether the tumor starts from the exocrine or endocrine gland of the pancreas. Tumors formed from the exocrine gland of the pancreas are much more common. These exocrine pancreatic tumors count for about 95 percent of pancreatic tumors. These tumors start in the exocrine cells that make pancreatic enzymes that help in digestion.

Pancreatic endocrine tumors constitute less than 5% of pancreatic tumors and are ACTH-secreting tumors. These tumors are also referred to as islet cell tumors, and most are benign. A special type of tumor (ampullary tumor) of the endocrine pancreatic tumors can occur where the bile duct from the liver and the pancreatic duct empty into the small intestine. Because this type of cancer often causes signs such as yellowing of the skin and eyes, it is usually found at an earlier stage than most pancreatic cancers. The chances of successful treatment are better for patients suffering from ampullary cancer.

According to the American Joint Committee on Cancer (AJCC) criteria, pancreatic cancers can be at one of four stages: stage I through IV, with stage IV indicating that the cancer has spread and is more serious. Specifically, stage I pancreatic cancer includes tumors which have not spread into certain proscribed sensitive areas and which have no involved regional nodes or distal metastasis. Stage II includes tumors which have spread into the duodenum, bile duct, or "peripancreatic" tissues and which have no involved regional nodes or distal metastasis. Stage III cancer includes tumors which may have or may not have spread into these areas and which have involved regional nodes, but which show no evidence of distal metastasis. Stage IVA includes tumors which have spread into the stomach, spleen, large bowel or the adjacent large vessels and which have involved regional nodes, but show no evidence of distal metastasis. Stage IVB includes pancreatic tumors of any kind with node status of any kind and with evidence of distal metastasis. Though referred to, this pancreatic cancer staging system is rarely used in its pure form because the stages do not fully match patient prognosis or treatment options. An alternative is the three stage classification (potentially resectable, locally advanced and metastatic), which is based on radiological findings. Other prognosis factors are also considered. The grade of the cancer which indicates how abnormal the cells look under the microscope is sometimes listed on a scale from G1 to G4, with G1 cancers looking the most like normal cells and having the best outlook. For patients who have surgery, the extent of the resection, i.e., whether or not all of the tumor is removed, is also important with regard to outlook. This is sometimes listed on a scale from R0 to R2 with R0 indicating that all of tumor that can be seen has been removed and R2 indicating that some tumor that can be seen cannot be removed.

D. Non-ACTH-Secreting Pancreatic Tumors

The methods disclosed herein are applicable for treating non-ACTH-secreting pancreatic tumors. After the diagnosis of pancreatic cancer, the tumor can be evaluated to determine the tumor origin, i.e., whether the tumor is an exocrine or neuroendocrine tumor, by histological analysis. In general, exocrine pancreatic tumors, which count for a majority of pancreatic tumors, are non-ACTH-secreting tumors and thus encompassed within the scope of the claims. In general, neuroendocrine pancreatic tumors are ACTH secreting pancreatic tumors and are not encompassed within the scope of the claims.

Alternatively, whether the tumor is a ACTH-secreting tumor can be determined by measuring the patients' ACTH level. This can be performed as an alternative or as an addition to the histological analysis. The types of samples that are suitable for ACTH determination can be serum, plasma, saliva, urine, or any other biological fluid taken from a subject. The level of ACTH can be measured using various methods, including but not limited to, immunoassays, e.g., competitive immunoassay, radioimmunoassay, immunofluorometric enzyme assay, and ELISA; competitive protein-binding assays; liquid chromatography (e.g., HPLC); and mass spectrometry, e.g., high-performance liquid chromatography/triple quadrupole-mass spectrometry (LC-MS/MS). Commercial kits for measuring ACTH are readily available, e.g., from Mayo clinic (Test ID: ACTH), Siemens Healthcare Global (Immulite® 2000 ACTH assay), and Roche Molecular Diagnostics (Catalog No. 03255751190).

The presence of an ACTH-secreting tumor in a patient is typically associated with a blood ACTH level being significantly higher than the normal reference value. Normal reference values vary depending on the assay method, type of sample, as well as the timing of sample collection because, like cortisol, ACTH in healthy individuals varies during a 24-hour period, reaching its highest level in the morning around 6-8 am and lowest at night around 11 pm. Various commercial kits provide the normal reference values in their testing protocols. For example, the normal range for ACTH using Mayo Clinc Test ID: ACTH is about 10-60 pg/mL. If the pancreatic cancer patient has an ACTH level that is significantly higher, e.g., at least 20%, 30%, 40%, 50%, 60%, 70% higher than the upper limit of the normal range—generally indicating the tumor is an ACTH secreting tumor,—he or she is not a subject encompassed by the claimed invention.

E. Glucocorticoid Receptor Modulators (GRM)

Generally, treatment of a non-ACTH-secreting pancreatic tumor can be provided by administering an effective amount of a chemotherapeutic agent in combination with an effective amount of a glucocorticoid receptor modulator (GRM) of any chemical structure or mechanism of action. In embodiments, the GRM is a selective GRM (SGRM). In embodiments, treatment of a non-ACTH-secreting pancreatic tumor can be provided by administering an effective amount of a chemotherapeutic agent in combination with an effective amount of a SGRM. In preferred embodiments, treatment of a non-ACTH-secreting pancreatic tumor can be provided by administering an effective amount of a chemotherapeutic agent in combination with an effective amount of a nonsteroidal SGRM. Provided herein are classes of exemplary GRMs, and in particular, exemplary nonsteroidal SGRMs, and specific members of such classes. However, one of skill in the art will readily recognize other related or unrelated GRMs and SGRMs that can be employed in the treatment methods described herein.

Nonsteroidal Glucocorticoid Receptor Modulators

Provided herein are classes of exemplary nonsteroidal glucocorticoid receptor modulators (nonsteroidal GRMs) and specific members of such classes that can be used for the method disclosed herein. However, one of skill in the art will readily recognize other related or unrelated glucocorticoid receptor modulators that can be employed in the treatment methods described herein. These include synthetic mimetics and analogs of proteins, including partially peptidic, pseudopeptidic and non-peptidic molecular entities. For example, oligomeric peptidomimetics useful in the invention include (α-β-unsaturated) peptidosulfonamides, N-substituted glycine derivatives, oligo carbamates, oligo urea peptidomimetics, hydrazinopeptides, oligosulfones and the like (See, e.g., Amour, Int. J. Pept. Protein Res. 43:297-304, 1994; de Bont, Bioorganic & Medicinal Chem. 4:667-672, 1996).

Examples of nonsteroidal GR modulators include the GR antagonist compounds disclosed in U.S. Pat. Nos. 5,696,127; 6,570,020; and 6,051,573; the GR antagonist compounds disclosed in US Patent Application 20020077356, the glucocorticoid receptor antagonists disclosed in Bradley et al., J. Med. Chem. 45, 2417-2424 (2002), e.g., 4α(S)-benzyl-2(R)-chloroethynyl-1,2,3,4,4a,9,10,10α(R)-octahydro-phenanthrene-2,7-diol ("CP 394531") and 4α(S)-benzyl-2(R)-prop-1-ynyl-1,2,3,4,4α,9,10,10α(R)-octahydro-phenanthrene-2,7-diol ("CP 409069"); and the compounds disclosed in PCT International Application No. WO 96/19458, which describes nonsteroidal compounds which are high-affinity, highly selective antagonists for steroid receptors, such as 6-substituted-1,2-dihydro-N-protected-quinolines.

For additional compounds that can be utilized in the methods of the invention and methods of identifying and making such compounds, see U.S. Pat. No. 4,296,206 (see above); U.S. Pat. No. 4,386,085 (see above); U.S. Pat. Nos. 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; and 5,616,458; and WO 96/19458, which describes nonsteroidal compounds which are high-affinity, highly selective modulators (antagonists) for steroid receptors, such as 6-substituted-1,2-dihydro N-1 protected quinolines.

In some embodiments, the combination therapy for treating cancer involves a GRM comprising a fused azadecalin structure, a GRM comprising a heteroaryl ketone fused azadecalin structure, or a GRM comprising an octahydro fused azadecalin structure.

Exemplary GRMs comprising a fused azadecalin structure include those described in U.S. Pat. Nos. 7,928,237; and 8,461,172 and can be prepared as disclosed therein. These patents are incorporated herein in their entirety. Such exemplary GRMs may be SGRMs. In some cases, the GRM comprising a fused azadecalin structure has the following structure:

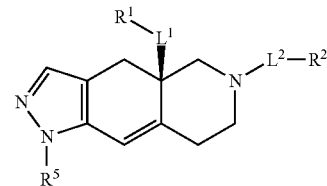

wherein $L^1$ and $L^2$ are members independently selected from a bond and unsubstituted alkylene;

$R^1$ is a member selected from unsubstituted alkyl, unsubstituted heteroalkyl, unsubstituted heterocycloalkyl, —$OR^{1A}$, —$NR^{1C}R^{1D}$, —C(O)$NR^{1C}R^{1D}$ and —C(O)$OR^{1A}$, wherein $R^{1A}$ is a member selected from hydrogen, unsubstituted alkyl and unsubstituted heteroalkyl, $R^{1C}$ and $R^{1D}$ are members independently selected from unsubstituted alkyl and unsubstituted heteroalkyl, wherein $R^{1C}$ and $R^{1D}$ are optionally joined to form an unsubstituted ring with the nitrogen to which they are attached, wherein said ring optionally comprises an additional ring nitrogen;

$R^2$ has the formula:

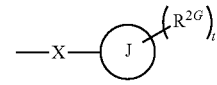

wherein $R^{2G}$ is a member selected from hydrogen, halogen, unsubstituted alkyl, unsubstituted heteroalkyl, unsubstituted cycloalkyl, unsubstituted heterocycloalkyl, —CN, and —$CF_3$;

J is phenyl;

t is an integer from 0 to 5;

X is —$S(O_2)$—; and $R^5$ is phenyl optionally substituted with 1-5 $R^{5A}$ groups, wherein $R^{5A}$ is a member selected from hydrogen, halogen, —$OR^{5A1}$, —$S(O_2)NR^{5A2}R^{5A3}$, —CN, and unsubstituted alkyl, wherein $R^{5A1}$ is a member selected from hydrogen and unsubstituted alkyl, and $R^{5A2}$ and $R^{5A3}$ are members independently selected from hydrogen and unsubstituted alkyl, or salts and isomers thereof.

Exemplary GRMs comprising a heteroaryl ketone fused azadecalin structure include those described in U.S. 2014/0038926, which can be prepared as disclosed therein, and is incorporated herein in its entirety. Such exemplary GRMs may be SGRMs. In some cases, the GRM comprising a heteroaryl ketone fused azadecalin structure has the following structure:

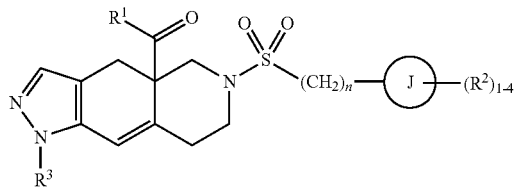

wherein
- $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;
- each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, —CN, N-oxide, $C_{3-8}$ cycloalkyl, and $C_{3-8}$ heterocycloalkyl;
- ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S;
- each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)OR^{2a}$, —$C(O)NR^{2a}R^{2b}$, —$SR^{2a}$, —$S(O)R^{2a}$, —$S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups;
- alternatively, two $R^2$ groups linked to the same carbon are combined to form an oxo group (=O);
- alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups;
- $R^{2a}$ and $R^{2b}$ are each independently selected from the group consisting of hydrogen and $C_{1-6}$ alkyl;
- each $R^{2c}$ is independently selected from the group consisting of hydrogen, halogen, hydroxy, $C_{1-6}$ alkoxy, $C_{1-6}$ haloalkoxy, —CN, and —$NR^{2a}R^{2b}$;
- each $R^{2d}$ is independently selected from the group consisting of hydrogen and $C_{1-6}$ alkyl, or two $R^{2d}$ groups attached to the same ring atom are combined to form (=O);
- $R^3$ is selected from the group consisting of phenyl and pyridyl, each optionally substituted with 1-4 $R^{3a}$ groups;
- each $R^{3a}$ is independently selected from the group consisting of hydrogen, halogen, and $C_{1-6}$ haloalkyl; and
- subscript n is an integer from 0 to 3;
- or salts and isomers thereof.

Exemplary GRMs comprising an octahydro fused azadecalin structure include those described in U.S. Pat. Pub. No. 20150148341 filed on Nov. 21, 2014 and can be prepared as described therein. The disclosure of U.S. Pat. Pub. No. 20150148341 is incorporated herein in their entirety. Such exemplary GRMs may be SGRMs. In some cases, the GRM comprising an octahydro fused azadecalin structure has the following structure:

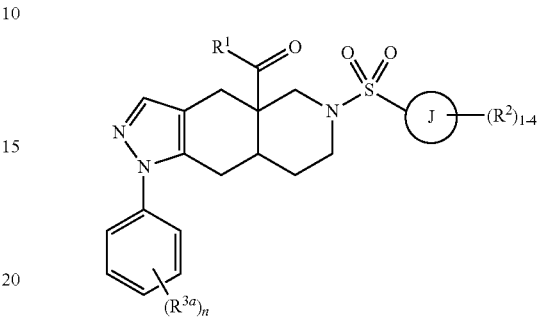

- $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;
- each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl;
- ring J is selected from the group consisting of an aryl ring and a heteroaryl ring having from 5 to 6 ring members and from 1 to 4 heteroatoms each independently selected from the group consisting of N, O and S;
- each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)OR^{2a}$, —$C(O)NR^{2a}R^{2b}$, —$SR^{2a}$, —$S(O)R^{2a}$, —$S(O)_2R^{2a}$, $C_{3-8}$ cycloalkyl, and $C_{3-8}$ heterocycloalkyl having from 1 to 3 heteroatoms each independently selected from the group consisting of N, O and S;
- alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups;
- $R^{2a}$, $R^{2b}$ and $R^{2c}$ are each independently selected from the group consisting of hydrogen and $C_{1-6}$ alkyl;
- each $R^{3a}$ is independently halogen; and
- subscript n is an integer from 0 to 3;
- or salts and isomers thereof.

F. Identifying Selective Glucocorticoid Receptor Modulators (SGRMs)

To determine whether a test compound is a SGRM, the compound is first subjected to assays to measure its ability to bind to the GR and inhibit GR-mediated activities, which determines whether the compound is a glucocorticoid receptor modulator. The compound, if confirmed to be a glucocorticoid receptor modulator, is then subjected to a selectivity test to determine whether the compound can bind specifically to GR as compared to non GR proteins, such as the estrogen receptor, the progesterone receptor, the androgen receptor, or the mineralocorticoid receptor. In one embodiment, a SGRM binds to GR at a substantially higher affinity, e.g., at least 10 times higher affinity, than to non-GR proteins. A SGRM may exhibit a 100-fold, 1000-fold or greater selectivity for binding to GR relative to binding to non GR proteins.

i. Binding

A test compounds' ability to bind to the glucocorticoid receptor can be measured using a variety of assays, for example, by screening for the ability of the test compound to compete with a glucocorticoid receptor ligand, such as dexamethasone, for binding to the glucocorticoid receptor. Those of skill in the art will recognize that there are a number of ways to perform such competitive binding assays. In some embodiments, the glucocorticoid receptor is pre-incubated with a labeled glucocorticoid receptor ligand and then contacted with a test compound. This type of competitive binding assay may also be referred to herein as a binding displacement assay. A decrease of the quantity of labeled ligand bound to glucocorticoid receptor indicates that the test compound binds to the glucocorticoid receptor. In some cases, the labeled ligand is a fluorescently labeled compound (e.g., a fluorescently labeled steroid or steroid analog). Alternatively, the binding of a test compound to the glucocorticoid receptor can be measured directly with a labeled test compound. This latter type of assay is called a direct binding assay.

Both direct binding assays and competitive binding assays can be used in a variety of different formats. The formats may be similar to those used in immunoassays and receptor binding assays. For a description of different formats for binding assays, including competitive binding assays and direct binding assays, see *Basic and Clinical Immunology* 7th Edition (D. Stites and A. Terr ed.) 1991; *Enzyme Immunoassay*, E. T. Maggio, ed., CRC Press, Boca Raton, Florida (1980); and "Practice and Theory of Enzyme Immunoassays," P. Tijssen, *Laboratory Techniques in Biochemistry and Molecular Biology*, Elsevier Science Publishers B. V. Amsterdam (1985), each of which is incorporated herein by reference.

In solid phase competitive binding assays, for example, the sample compound can compete with a labeled analyte for specific binding sites on a binding agent bound to a solid surface. In this type of format, the labeled analyte can be a glucocorticoid receptor ligand and the binding agent can be glucocorticoid receptor bound to a solid phase. Alternatively, the labeled analyte can be labeled glucocorticoid receptor and the binding agent can be a solid phase glucocorticoid receptor ligand. The concentration of labeled analyte bound to the capture agent is inversely proportional to the ability of a test compound to compete in the binding assay.

Alternatively, the competitive binding assay may be conducted in the liquid phase, and any of a variety of techniques known in the art may be used to separate the bound labeled protein from the unbound labeled protein. For example, several procedures have been developed for distinguishing between bound ligand and excess bound ligand or between bound test compound and the excess unbound test compound. These include identification of the bound complex by sedimentation in sucrose gradients, gel electrophoresis, or gel isoelectric focusing; precipitation of the receptor-ligand complex with protamine sulfate or adsorption on hydroxylapatite; and the removal of unbound compounds or ligands by adsorption on dextran-coated charcoal (DCC) or binding to immobilized antibody. Following separation, the amount of bound ligand or test compound is determined.

Alternatively, a homogenous binding assay may be performed in which a separation step is not needed. For example, a label on the glucocorticoid receptor may be altered by the binding of the glucocorticoid receptor to its ligand or test compound. This alteration in the labeled glucocorticoid receptor results in a decrease or increase in the signal emitted by label, so that measurement of the label at the end of the binding assay allows for detection or quantitation of the glucocorticoid receptor in the bound state. A wide variety of labels may be used. The component may be labeled by any one of several methods. Useful radioactive labels include those incorporating $^3H$, $^{125}I$, $^{35}S$ $^{14}C$, or $^{32}P$. Useful non-radioactive labels include those incorporating fluorophores, chemiluminescent agents, phosphorescent agents, electrochemiluminescent agents, and the like. Fluorescent agents are especially useful in analytical techniques that are used to detect shifts in protein structure such as fluorescence anisotropy and/or fluorescence polarization. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference in its entirety for all purposes. The label may be coupled directly or indirectly to the desired component of the assay according to methods well known in the art. In some cases, a test compound is contacted with a GR in the presence of a fluorescently labeled ligand (e.g., a steroid or steroid analog) with a known affinity for the GR, and the quantity of bound and free labeled ligand is estimated by measuring the fluorescence polarization of the labeled ligand.

ii. Activity

1) HepG2 Tyrosine Aminotransferase (TAT) Assay

Compounds that have demonstrated the desired binding affinity to GR are tested for their activity in inhibiting GR mediated activities. The compounds are typically subject to a Tyrosine Aminotransferase Assay (TAT assay), which assesses the ability of a test compound to inhibit the induction of tyrosine aminotransferase activity by dexamethasone. See Example 1. GR modulators that are suitable for the method disclosed herein have an $IC_{50}$ (half maximal inhibition concentration) of less than 10 micromolar. Other assays, including but not limited to those described below, can also be deployed to confirm the GR modulation activity of the compounds.

2) Cell-Based Assays

Cell-based assays which involve whole cells or cell fractions containing glucocorticoid receptors can also be used to assay for a test compound's binding or modulation of activity of the glucocorticoid receptor. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemia cells, Burkitt's lymphoma cells, tumor cells (including mouse mammary tumor virus cells), endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, the glucocorticoid receptor can be expressed in cells that do not express an endogenous version of the glucocorticoid receptor.

In some cases, fragments of the glucocorticoid receptor, as well as protein fusions, can be used for screening. When molecules that compete for binding with the glucocorticoid receptor ligands are desired, the GR fragments used are fragments capable of binding the ligands (e.g., dexamethasone). Alternatively, any fragment of GR can be used as a target to identify molecules that bind the glucocorticoid receptor. Glucocorticoid receptor fragments can include any fragment of, e.g., at least 20, 30, 40, 50 amino acids up to a protein containing all but one amino acid of glucocorticoid receptor.

In some embodiments, a reduction in signaling triggered by glucocorticoid receptor activation is used to identify glucocorticoid receptor modulators. Signaling activity of the glucocorticoid receptor can be determined in many ways. For example, downstream molecular events can be monitored to determine signaling activity. Downstream events include those activities or manifestations that occur as a result of stimulation of a glucocorticoid receptor. Exemplary downstream events useful in the functional evaluation of transcriptional activation and antagonism in unaltered cells include upregulation of a number of glucocorticoid response element (GRE)-dependent genes (PEPCK, tyrosine amino transferase, aromatase). In addition, specific cell types susceptible to GR activation may be used, such as osteocalcin expression in osteoblasts which is downregulated by glucocorticoids; primary hepatocytes which exhibit glucocorticoid mediated upregulation of PEPCK and glucose-6-phosphate (G-6-Pase)). GRE-mediated gene expression has also been demonstrated in transfected cell lines using well-known GRE-regulated sequences (e.g., the mouse mammary tumor virus promoter (MMTV) transfected upstream of a reporter gene construct). Examples of useful reporter gene constructs include luciferase (luc), alkaline phosphatase (ALP) and chloramphenicol acetyl transferase (CAT). The functional evaluation of transcriptional repression can be carried out in cell lines such as monocytes or human skin fibroblasts. Useful functional assays include those that measure IL-1 beta stimulated TL-6 expression; the downregulation of collagenase, cyclooxygenase-2 and various chemokines (MCP-1, RANTES); LPS stimulated cytokine release, e.g., TNFα; or expression of genes regulated by NFkB or AP-1 transcription factors in transfected cell-lines.

Compounds that are tested in whole-cell assays can also be tested in a cytotoxicity assay. Cytotoxicity assays are used to determine the extent to which a perceived effect is due to non-glucocorticoid receptor binding cellular effects. In an exemplary embodiment, the cytotoxicity assay includes contacting a constitutively active cell with the test compound. Any decrease in cellular activity indicates a cytotoxic effect.

3) Additional Assays

Further illustrative of the many assays which can be used to identify compositions utilized in the methods of the invention, are assays based on glucocorticoid activities in vivo. For example, assays that assess the ability of a putative GR modulator to inhibit uptake of 3H-thymidine into DNA in cells which are stimulated by glucocorticoids can be used. Alternatively, the putative GR modulator can complete with 3H-dexamethasone for binding to a hepatoma tissue culture GR (see, e.g., Choi, et al., *Steroids* 57:313-318, 1992). As another example, the ability of a putative GR modulator to block nuclear binding of 3H-dexamethasone-GR complex can be used (Alexandrova et al., *J. Steroid Biochem. Mol. Biol.* 41:723-725, 1992). To further identify putative GR modulators, kinetic assays able to discriminate between glucocorticoid agonists and modulators by means of receptor-binding kinetics can also be used (as described in Jones, *Biochem J.* 204:721-729, 1982).

In another illustrative example, the assay described by Daune, Molec. Pharm. 13:948-955, 1977; and in U.S. Pat. No. 4,386,085, can be used to identify anti-glucocorticoid activity. Briefly, the thymocytes of adrenalectomized rats are incubated in nutritive medium containing dexamethasone with the test compound (the putative GR modulator) at varying concentrations. $^3$H-uridine is added to the cell culture, which is further incubated, and the extent of incorporation of radiolabel into polynucleotide is measured. Glucocorticoid agonists decrease the amount of $^3$H-uridine incorporated. Thus, a GR modulator will oppose this effect.

iii. Selectivity

The GR modulators selected above are then subject to a selectivity assay to determine whether they are SGRMs. Typically, selectivity assays include testing a compound that binds glucocorticoid receptor in vitro for the degree of binding to non-glucocorticoid receptor proteins. Selectivity assays may be performed in vitro or in cell based systems, as described above. Binding may be tested against any appropriate non-glucocorticoid receptor protein, including antibodies, receptors, enzymes, and the like. In an exemplary embodiment, the non-glucocorticoid receptor binding protein is a cell-surface receptor or nuclear receptor. In another exemplary embodiment, the non-glucocorticoid receptor protein is a steroid receptor, such as estrogen receptor, progesterone receptor, androgen receptor, or mineralocorticoid receptor.

The selectivity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606,021; 5,696,127; 5,215,916; 5,071,773). Such an analysis can be performed using either a direct binding assay or by assessing competitive binding to the purified GR or MR in the presence of a known ligand. In an exemplary assay, cells that stably express the glucocorticoid receptor or mineralocorticoid receptor (see, e.g., U.S. Pat. No. 5,606, 021) at high levels are used as a source of purified receptor. The affinity of the ligand for the receptor is then directly measured. Those GR modulators that exhibit at least a 10 fold, 100-fold higher affinity, often 1000-fold, for the GR relative to the MR are then selected for use in the methods of the invention.

The selectivity assay may also include assaying the ability to inhibit GR-mediated activities, but not MR-mediated activities. One method of identifying such a GR-specific modulator is to assess the ability of an antagonist to prevent activation of reporter constructs using transfection assays (see, e.g., Bocquel et al, J. Steroid Biochem Molec. Biol. 45:205-215, 1993; U.S. Pat. Nos. 5,606,021, 5,929,058). In an exemplary transfection assay, an expression plasmid encoding the receptor and a reporter plasmid containing a reporter gene linked to receptor-specific regulatory elements are cotransfected into suitable receptor-negative host cells. The transfected host cells are then cultured in the presence and absence of a hormone, such as cortisol or an analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. GR modulators that exhibits at least a 100-fold, often 1000-fold or greater, activity towards the GR relative to the MR, PR, or AR are then selected for use in the methods disclosed herein.

An exemplar nonsteroidal SGRM that can be used in the methods disclosed herein is CORT 125134, i.e., (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, which has the following structure:

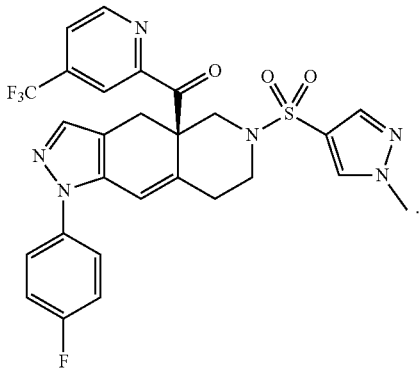 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

Another exemplar nonsteroidal SGRM that can be used in the methods disclosed herein is CORT125281, i.e., ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl) methanone, which has the following structure:

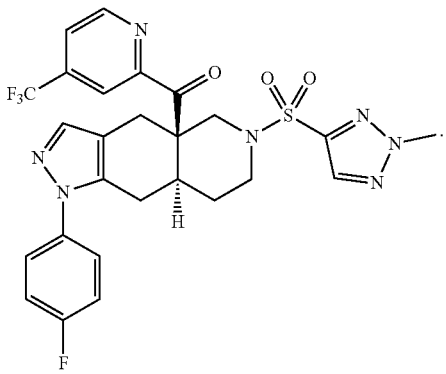 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

G. Pharmaceutical Compositions and Administration

In embodiments, the present invention provides a pharmaceutical composition for treating non-ACTH-secreting pancreatic tumors, the pharmaceutical composition including a pharmaceutically acceptable excipient and a GRM. In some embodiments, the pharmaceutical composition includes a pharmaceutically acceptable excipient and a SGRM. In preferred embodiments, the pharmaceutical composition includes a pharmaceutically acceptable excipient and a nonsteroidal SGRM.

GRMs and SGRMs (as used herein, GRMs and SGRMs include nonsteroidal GRMs and nonsteroidal SGRMS), can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. GRMs and SGRMs can also be administered by injection, that is, intravenously, intramuscularly, intracutaneously, subcutaneously, intraduodenally, or intraperitoneally. Also, GRMs and SGRMs can be administered by inhalation, for example, intranasally. Additionally, GRMs and SGRMs can be administered transdermally. Accordingly, the present invention also provides pharmaceutical compositions including a pharmaceutically acceptable carrier or excipient and a GRM or SGRM.

For preparing pharmaceutical compositions from GRMs and SGRMs, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

In powders, the carrier is a finely divided solid, which is in a mixture with the finely divided active component, a GRM or SGRM. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR modulator mixed with a filler or binders such as lactose or starches, lubricants such as talc or magnesium stearate, and, optionally, stabilizers. In soft capsules, the GR modulator compounds may be dissolved or suspended in suitable liquids, such as fatty oils, liquid paraffin, or liquid polyethylene glycol with or without stabilizers.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a SGRM in a vegetable oil, such as *arachis* oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

GRMs and SGRMs can be delivered by transdermally, by a topical route, formulated as applicator sticks, solutions, suspensions, emulsions, gels, creams, ointments, pastes, jellies, paints, powders, and aerosols.

GRMs and SGRMs can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use In another embodiment, the formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component, a GRM or SGRM. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 6000 mg, most typically 50 mg to 500 mg. Suitable dosages also include about 1 mg, 5, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, or 2000 mg, according to the particular application and the potency of the active component. The composition can, if desired, also contain other compatible therapeutic agents.

Single or multiple administrations of formulations can be administered depending on the dosage and frequency as required and tolerated by the patient. The formulations should provide a sufficient quantity of active agent to effectively treat the disease state. Thus, in one embodiment, the pharmaceutical formulation for oral administration of a GRM is in a daily amount of between about 0.01 to about 150 mg per kilogram of body weight per day (mg/kg/day). In some embodiments, the daily amount is from about 1.0 to 100 mg/kg/day, 5 to 50 mg/kg/day, 10 to 30 mg/kg/day, and 10 to 20 mg/kg/day. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable formulations will be known or apparent to those skilled in the art and are described in more detail in such publications as Remington's, supra. See also Nieman, In "Receptor Mediated Antisteroid Action," Agarwal, et al., eds., De Gruyter, New York (1987).

The duration of treatment with a GRM or SGRM to reduce the tumor load of non-ACTH-secreting pancreatic tumor or otherwise ameliorate the symptoms of the tumor can vary according to the severity of the condition in a subject and the subject's response to GRMs or SGRMs. In some embodiments, GRMs and SGRMs can be administered for a period of about 1 week to 104 weeks (2 years), more typically about 6 weeks to 80 weeks, most typically about 9 to 60 weeks. Suitable periods of administration also include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 104 weeks. Suitable periods of administration also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, 100, and 104 weeks. Generally administration of a GRM or SGRM should be continued until clinically significant reduction or amelioration is observed. Treatment with the GRM or SGRM in accordance with the invention may last for as long as two years or even longer.

In some embodiments, administration of a GRM or SGRM is not continuous and can be stopped for one or more periods of time, followed by one or more periods of time where administration resumes. Suitable periods where administration stops include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 100 weeks. Suitable periods where administration stops also include 5, 6, 7, 8,9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, and 100 weeks.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR modulator and disease or condition treated.

SGRMs can be used in combination with other active agents known to be useful in modulating a glucocorticoid receptor, or with adjunctive agents that may not be effective alone, but may contribute to the efficacy of the active agent.

In some embodiments, co-administration includes administering one active agent, a GRM or SGRM, within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

After a pharmaceutical composition including a GR modulator of the invention has been formulated in an acceptable carrier, it can be placed in an appropriate container and labeled for treatment of an indicated condition. For administration of a GRM or SGRM, such labeling would include, e.g., instructions concerning the amount, frequency and method of administration.

The pharmaceutical compositions of the present invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

H. Chemotherapeutic Agents

Chemotherapeutic agents suitable for use in combination with the SGRM of the invention include agents that have the property of killing cancer cells or inhibiting cancer cell growth, such as those disclosed in US Pat. Pub. No. 20150218274, and also http://chemocare.com/chemotherapy/what-is-chemotherapy/types-of-chemotherapy-.aspx. These agents include, but are not limited to antimicrotubule agents (e.g., taxanes and *vinca* alkaloids), topoisomerase inhibitors and antimetabolites (e.g., nucleoside analogs acting as such, for example, Gemcitabine), mitotic inhibitors, alkylating agents, antimetabolites, antitumor antibiotics, mitotic inhibitors, anthracyclines, intercalating agents, agents capable of interfering with a signal transduction pathway, agents that promote apoptosis, proteosome inhibitors, and the like.

Alkylating agents are most active in the resting phase of the cell. These types of drugs are cell-cycle non-specific. Exemplary alkylating agents that can be used in combination with the SGRM of the invention include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Antitumor antibiotics are chemo agents obtained from natural products produced by species of the soil fungus *Streptomyces*. These drugs act during multiple phases of the cell cycle and are considered cell-cycle specific. There are several types of antitumor antibiotics, including but are not limited to Anthracyclines (e.g., Doxorubicin, Daunorubicin, Epirubicin, Mitoxantrone, and Idarubicin), Chromomycins (e.g., Dactinomycin and Plicamycin), Mitomycin and Bleomycin.

Antimetabolites are types of chemotherapy treatments that are cell-cycle specific. When the cells incorporate these antimetabolite substances into the cellular metabolism, they are unable to divide. These class of chemotherapy agents include folic acid antagonists such as Methotrexate; pyrimidine antagonists such as 5-Fluorouracil, Floxuridine, Cytarabine, Capecitabine, and Gemcitabine; purine antagonists such as 6-Mercaptopurine and 6-Thioguanine; Adenosine deaminase inhibitors such as Cladribine, Fludarabine, Nelarabine and Pentostatin.

Exemplary anthracyclines that can be used in combination with the SGRM of the invention include, e.g., doxorubicin (Adriamycin® and Rubex®); Bleomycin (Lenoxane®); Daunorubicin (daunorubicin hydrochloride, daunomycin, and rubidomycin hydrochloride, Cerubidine®); Daunorubicin liposomal (daunorubicin citrate liposome, DaunoXome®); Mitoxantrone (DHAD, Novantrone®); Epirubicin (Ellence); Idarubicin (Idamycin®, Idamycin PFS®); Mitomycin C (Mutamycin®); Geldanamycin; Herbimycin; Ravidomycin; and Desacetylravidomycin.

Antimicrotubule agents include *vinca* alkaloids and taxanes. Exemplary *vinca* alkaloids that can be used in combination with the SGRM of the invention include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®). Exemplary taxanes that can be used in combination with the SGRM of the invention include, but are not limited to paclitaxel and docetaxel. Non-limiting examples of paclitaxel agents include nanoparticle albumin-bound paclitaxel (ABRAXANE, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., Biopolymers (2007) 87:225-230), and glucose-conjugated paclitaxel (e.g., 2'-paclitaxel methyl 2-glucopyranosyl succinate, see Liu et al., Bioorganic & Medicinal Chemistry Letters (2007) 17:617-620).

Exemplary proteosome inhibitors that can be used in combination with the SGRM of the invention, include, but are not limited to, Bortezomib (Velcade®); Carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamid-o)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(−2R)-2-methyl-2-oxiranyl]-2-oxo-1-(phenylmethyl)ethyl]-L-serinamide (ONX-0912).

In some embodiments, the chemotherapeutic agent is selected from the group consisting of chlorambucil, cyclophosphamide, ifosfamide, melphalan, streptozocin, carmustine, lomustine, bendamustine, uramustine, estramustine, carmustine, nimustine, ranimustine, mannosulfan busulfan, dacarbazine, temozolomide, thiotepa, altretamine, 5-fluorouracil (5-FU), 6-mercaptopurine (6-MP), capecitabine, cytarabine, floxuridine, fludarabine, gemcitabine, hydroxyurea, methotrexate, pemetrexed, daunorubicin, doxorubicin, epirubicin, idarubicin, SN-38, ARC, NPC, camptothecin, topotecan, 9-nitrocamptothecin, 9-aminocamptothecin, rubifen, gimatecan, diflomotecan, BN80927, DX-895 1f, MAG-CPT, amsacrine, etoposide, etoposide phosphate, teniposide, doxorubicin, paclitaxel, docetaxel, gemcitabine, accatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephalomannine, gemcitabine, Irinotecan, albumin-bound paclitaxel, Oxaliplatin, Capecitabine, Cisplatin, docetaxel, irinotecan liposome, and etoposide, and combinations thereof.

In certain embodiments, the chemotherapeutic agent is administered at a dose and a schedule that may be guided by doses and schedules approved by the U.S. Food and Drug Administration (FDA) or other regulatory body, subject to empirical optimization. In some cases, the chemotherapeutic agent is administered at a dose of about 100 to 1000 mg, e.g., about 200 mg to 800 mg, about 300 mg to 700 mg, or about 400 mg to 600 mg, e.g., about 200 mg, 300 mg, 400 mg, 500 mg, 600 mg, or 700 mg. The dosing schedule can vary from, e.g. every week, every five days, every four days, every other day to daily, twice, or three times a day. In one embodiment, the chemotherapeutic agent is administered at an oral dose or an intravenous dose from about 100 mg to 600 mg daily, e.g., about 100 mg, 200 mg, 260 mg, 300 mg, 400 mg, or 600 mg daily, every other day or every four days for the whole or a portion of the treatment period. In some embodiments, the chemotherapeutic agent is a taxane and can be used at any standard dose, for example those taxane doses approved by the FDA, in accordance with the methods of the invention. In various embodiments, the taxane is nab-paclitaxel, which is administered at a dose ranging from 80 mg to 125 mg per square meter of body-surface area as an intravenous infusion over 30 minutes on days 1, 8, and 15 of every 28-day cycle.

In still further embodiments, more than one chemotherapeutic agent may be administered simultaneously, or sequentially in any order during the entire or portions of the treatment period. The two agents may be administered following the same or different dosing regimens.

I. Combination Therapies

Various combinations with a GRM or SGRM and a chemotherapeutic agent (or a combination of such agents and compounds) may be employed to reduce the tumor load in the patient. By "combination therapy" or "in combination with", it is not intended to imply that the therapeutic agents must be administered at the same time and/or formulated for delivery together, although these methods of delivery are within the scope described herein. The GRM or SGRM and the chemotherapeutic agent can be administered following the same or different dosing regimen. In some embodiments, the GRM or SGRM and the chemotherapeutic agent is administered sequentially in any order during the entire or portions of the treatment period. In some embodiments, the GRM or SGRM and the anticancer agent is administered simultaneously or approximately simultaneously (e.g., within about 1, 5, 10, 15, 20, or 30 minutes of each other). Non-limiting examples of combination therapies are as follows, with administration of the GRM or SGRM and the chemo agent for example, GRM or SGRM is "A" and the anticancer agent or compound, given as part of an chemo therapy regime, is "B":

A/B/AB/A/BB/B/AA/A/BA/B/BB/A/AA/B/B/B    B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the therapeutic compounds or agents to a patient will follow general protocols for the administration of such compounds, taking into account the toxicity, if any, of the therapy. Surgical intervention may also be applied in combination with the described therapy.

The present methods involved can be combined with other means of treatment such as surgery, radiation, targeted therapy, immunotherapy, use of growth factor inhibitors, or anti-angiogenesis factors.

J. Evaluate Improvements in Reducing Tumor Loads

The GRM or SGRM therapy disclosed herein can reduce the tumor load and confer beneficial clinical outcome to patients having a non-ACTH-secreting pancreatic tumor. Methods for measuring these responses are well-known to skilled artisans in the field of cancer therapy, e.g., as described in the Response Evaluation Criteria in Solid Tumors ("RECIST") guidelines, available at ctep.cancer.gov/protocolDevelopment/docs/recist_guideline.pdf.

In one approach, the tumor load is measured by assaying expression of tumor-specific biomarkers. This approach is especially useful for metastatic tumors. A tumor-specific biomarker is a protein or other molecule that is unique to cancer cells or is much more abundant in them as compared to non-cancer cells. Useful biomarkers for pancreatic cancer are known, for example, CaSM gene, as disclosed in U.S. Pat. No. 6,720,413, and p53, MUC1, Rad51, DEAD-box protein 48, Calreticulin, Vimentin, Osteopontin, etc. as disclosed in Misek et al., J. Natl. Compr. Canc. Netw. 2007; 5(10): 1034-1041. In some cases, the level of CA19-9, which are foreign substances released by pancreatic tumor cells, is evaluated throughout the treatment—decreasing in CA 19-9 values may indicate that treatment is effective and that the tumor or amount of cancer in the body is decreasing. A decline in CA 19-9 levels after treatment for pancreatic cancer followed by a rise later may suggest tumor recurrence or progression. See, https://www.pancan.org/facing-pancreatic-cancer/diagnosis/CA19-9.

Methods of measuring the expression levels of a tumor-specific genetic marker are well known. In some embodiments, mRNA of the genetic marker is isolated from the blood sample or a tumor tissue and real-time reverse transcriptase-polymerase chain reaction (RT-PCR) is performed to quantify expression of the genetic marker. In some embodiments, western blots or immunohistochemistry analysis are performed to evaluate the protein expression of the tumor-specific genetic marker. Typically the levels of the tumor-specific genetic marker are measured in multiple samples taken over time of the combination therapy of the invention, and a decrease in levels correlates with a reduction in tumor load.

In another approach, the reduction of tumor load by the combination therapy disclosed herein is shown by a reduction in tumor size or a reduction of amount of cancer in the body. Measuring tumor size is typically achieved by imaging-based techniques. For example, computed tomography (CT) scan can provide accurate and reliable anatomic information about not only tumor shrinkage or growth but also progression of disease by identifying either growth in existing lesions or the development of new lesions or tumor metastasis.

In yet another approach, a reduction of tumor load can be assessed by functional and metabolic imaging techniques. These techniques can provide earlier assessment of therapy response by observing alterations in perfusion, oxygenation and metabolism. For example, $^{18}$F-FDG PET uses radiolabelled glucose analogue molecules to assess tissue metabolism. Tumors typically have an elevated uptake of glucose, a change in value corresponding to a decrease in tumor tissue metabolism indicates a reduction in tumor load. Similar imaging techniques are disclosed in Kang et al., Korean J. Radiol. (2012) 13(4) 371-390.

A patient receiving the therapy disclosed herein may exhibit varying degrees of tumor load reduction. In some cases, a patient can exhibit a Complete Response (CR), also referred to as "no evidence of disease (NED)". CR means all detectable tumor has disappeared as indicated by tests, physical exams and scans. In some cases, a patient receiving the combination therapy disclosed herein can experience a Partial Response (PR), which roughly corresponds to at least a 50% decrease in the total tumor volume but with evidence of some residual disease still remaining. In some cases the residual disease in a deep partial response may actually be dead tumor or scar so that a few patients classified as having a PR may actually have a CR. Also many patients who show shrinkage during treatment show further shrinkage with continued treatment and may achieve a CR. In some cases, a patient receiving the combination therapy can experience a Minor Response (MR), which roughly means a small amount of shrinkage that is more than 25% of total tumor volume but less than the 50% that would make it a PR. In some cases, a patient receiving the combination therapy can exhibit Stable Disease (SD), which means the tumors stay roughly the same size, but can include either a small amount of growth (typically less than 20 or 25%) or a small amount of shrinkage (Anything less than a PR unless minor responses are broken out. If so, then SD is defined as typically less 25%).

Desired beneficial or desired clinical results from the combination therapy may also include e. g., reduced (i.e., slowing to some extent and/or stop) cancer cell infiltration into peripheral organs; inhibited (i.e., slowing to some extent and/or stop) tumor metastasis; increased response rates (RR); increased duration of response; relieved to some extent one or more of the symptoms associated with the cancer; decreased dose of other medications required to treat the disease; delayed progression of the disease; and/or prolonged survival of patients and/or improved quality of life. Methods for evaluating these effects are well known and/or disclosed in, e.g., cancerguide.org/endpoints.html and RECIST guidelines, supra.

All patents, patent publications, publications, and patent applications cited in this specification are hereby incorporated by reference herein in their entireties as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

Example 1. HEPG2 Tyrosine Aminotransferase (TAT) Assay

The following protocol describes an assay for measuring induction of TAT by dexamethasone in HepG2 cells (a human liver hepatocellular carcinoma cell line; ECACC, UK). HepG2 cells are cultured using MEME media supplemented with 10% (v/v) foetal bovine serum; 2 mM L-glutamine and 1% (v/v) NEAA at 37° C., 5%/95% (v/v) $CO_2$/air. The HepG2 cells are then be counted and adjusted to yield a density of $0.125 \times 10^6$ cells/ml in RPMI 1640 without phenol red, 10% (v/v) charcoal stripped FBS, 2 mM L-glutamine and seeded at 25,000 cells/well in 200 µl into 96 well, sterile, tissue culture micro titre plates, and incubated at 37° C., 5% $CO_2$ for 24 hours.

Growth media are then removed and replaced with assay media {RPMI 1640 without phenol red, 2 mM L-glutamine+ 10 µM forskolin}. Test compounds are then screened against a challenge of 100 nM dexamethasone. Compounds are then be serially half log diluted in 100% (v/v) dimethylsulfoxide from a 10 mM stock. Then an 8-point half-log dilution curve are generated followed by a 1:100 dilution into assay media to give a 10× final assay of the compound concentration, this results in final assay of the compound concentration that ranged 10 to 0.003 µM in 0.1% (v/v) dimethylsulfoxide.

Test compounds are pre-incubated with cells in microtitre plates for 30 minutes at 37° C., 5/95 (v/v) $CO_2$/air, before the addition of 100 nM dexamethasone and then subsequently for 20 hours to allow optimal TAT induction.

HepG2 cells are then be lysed with 30 µl of cell lysis buffer containing a protease inhibitor cocktail for 15 minutes at 4° C. 155 µl of substrate mixture can then be added containing 5.4 mM Tyrosine sodium salt, 10.8 mM alpha ketoglutarate and 0.06 mM pyridoxal 5' phosphate in 0.1 M potassium phosphate buffer (pH 7.4). After 2 hours incubation at 37° C. the reaction can be terminated by the addition of 15 µl of 10 M aqueous potassium hydroxide solution, and the plates incubated for a further 30 minutes at 37° C. The TAT activity product can be measured by absorbance at λ 340 nm.

$IC_{50}$ values can be calculated by plotting % inhibition (normalised to 100 nM dexamethasone TAT stimulation) v. compound concentration and fitting the data to a 4 parameter logistic equation. $IC_{50}$ values can converted to Ki (equilibrium dissociation constant) using the Cheng and Prusoff equation, assuming the antagonists were competitive inhibitors with respect to dexamethasone.

Example 2. Reducing Tumor Growth Using the Combination Therapy of CORT 125134 and a Chemotherapeutic Agent Human Pancreatic carcinoma cells (MIA-PaCa-2) were purchased from the American Type Cell Collection (ATCC). The cells were grown in Dulbecco's Modified Eagle's Medium (DMEM) containing 10% (v/v) heat inactivated fetal calf serum and 2.5% horse serum at 37° C. Suspensions of the cells were injected subcutaneously into the left flank of 5-6 week old immunocompromised female mice (Balbc/c nude), 3 million cells per mouse. Tumors were allowed to grow until they reach a volume of 100-200 cubic millimeters ($mm^3$). Mice were then grouped into four groups, ten (10) per group, and treated with compounds or vehicle as follows. Vehicle or paclitaxel was administered intravenously and SGRMs, i.e., CORT25134 and CORT125281, were administered orally. SGRMs were administered in vehicle ((10% dimethyl sulfoxide (DMSO), 0.1% Tween 80 (polyethylene glycol sorbitan monooleate (polysorbate 80)) and 89.9% hydroxypropyl methylcellulose (HPMC) (0.5%)). Group 1 was dosed with the compound vehicle (10% DMSO, 0.1% Tween 80 and 89.9% HPMC (0.5%)) daily. Group 2 was dosed with paclitaxel at 7.5 mg/kg, every four days ("Q4D"). Group 3 was dosed with both paclitaxel at 7.5 mg/kg Q4D and CORT125134 at 30 mg/kg on the day prior to and the same day as the day paclitaxel was administered. Group 4 was dosed with both paclitaxel at 7.5 mg/kg Q4D and CORT125281 at 30 mg/kg on the day prior to and the same day as the day paclitaxel was administered.

The longest (L) and shortest (S) diameters of the tumors were measured three times a week with electronic calipers and tumor volume was calculated using the formula V=0.5 a×b, where a and b are the long and short diameters of the tumor, respectively. The tumor growth data are shown in The FIGURE, in which the mean tumor volume as compared to the mean pre-dosing tumor volume for each group of mice is plotted against the number of days of tumor growth since initiation of the treatment. The result shows that the combination of paclitaxel and SGRM, i.e., CORT125134 or CORT125281, are superior to the paclitaxel group in reducing tumor growth. Mice treated with the combination of the paclitaxel and CORT125134 showed the most significant tumor growth reduction.

Example 3. Treating a Patient Having Pancreatic Cancer with SGRM and a Chemotherapeutic Agent A typical pancreatic patient may complain of upper abdomen pain that typically radiates to the back. Such a patient may experience loss of appetite, nausea and vomiting episodes, and may suffer significant weight loss. A CT scan may show the presence of a tumor in the pancreas. The presence of an exocrine pancreatic tumor may be confirmed by histological analysis. Blood ACTH level may be within the normal range for ACTH. Such a patient may be treated with CORT125134 at a dose of 200 mg once a day for eight weeks in combination with an intravenous infusion of nab-paclitaxel at a dose of 80 mg per square meter of body-surface area as an intravenous infusion over 30 minutes on days 1, 8, and 15 of every 28-day cycle. Tumor load may be monitored using enhanced MRI before, during and after such treatment. Imaging results may indicate that the size of the tumor gradually decreases; such reduction may be more than 50% at the end of the treatment period.

Example 4. Treatment of a Patient Having Advanced Pancreatic Cancer with SGRM and a Chemotherapeutic Agent Following Tumor Progression on Multiple Prior Chemotherapeutic Treatments A 39-year-old patient with a diagnosis of metastatic adenocarcinoma of the pancreas participated in a clinical study evaluating the efficacy of daily administration of 100 mg of the GR antagonist CORT125134 in combination with nab-paclitaxel infusions weekly for three out of four weeks per cycle. A tumor tissue sample obtained during or prior to the patient's previous treatments was found by immunohistochemistry to have high GR expression, with 90 percent of the cells staining for GR and with a large percentage staining with high intensity. Prior to receiving this combined GR antagonist and nab-paclitaxel treatment, the patient had previously received treatment with multiple lines of chemotherapy: gemcitabine monotherapy; eight months of combination chemotherapy treatment with 5-fluorouracil, leucovorin, irinotecan and oxaliplatin (FOLFIRINOX treatment); five months of treatment with gemcitabine combined with nab-paclitaxel; and four months of combination chemotherapy treatment with 5-fluorouracil, leucovorin, and irinotecan hydrochloride (FOLFIRI treatment). These prior treatments were unsuccessful: the patient's cancer progressed despite these prior chemotherapy treatments.

This patient has so far received 8 months (8 cycles) of the combined treatment of daily 100 mg CORT125134 in combination with nab-paclitaxel infusions weekly for three out of four weeks per cycle. The patient has experienced a partial response (PR) to this treatment by the combination of CORT125134 and nab-paclitaxel, and has tolerated the treatment reasonably well. On the third month/cycle of treatment, the tumor volume was observed to be reduced by approximately 40% as compared to the tumor volume measured at the start of the study (volume measurements were made using computer tomography (CT) scans). When scanned again one month later, the tumor volume was still reduced by approximately 40% compared to baseline volume, thus confirming the PR status. A further scan during the seventh month of treatment was also performed, and the patient was found to have retained the 40% reduction (compared to baseline) in tumor volume. The patient remains on the treatment, and continues to tolerate the treatment well.

In summary, this patient with advanced pancreatic cancer has exhibited an excellent clinical response by achieving a sustained partial response during 8 months of the treatment. The patient has tolerated the treatment with CORT125134 and nab-paclitaxel well, and continues to receive further cycles of the treatment. It is notable that this patient had previously experienced significant growth/progression of her tumor during prior chemotherapies, which included treatment with nab-paclitaxel and gemcitabine in combination. Thus, the combination of CORT125134 daily 100 mg with nab-paclitaxel infusions weekly for three out of four weeks per cycle in the treatment of advanced pancreatic cancer in this patient produced regression in tumor volume and provided a more durable response than had treatment with nab-paclitaxel plus gemcitabine.

What is claimed is:

1. A method of treating a subject hosting a non-ACTH-secreting pancreatic tumor, the method comprising administering to the subject an effective amount of an antimicrotubule agent selected from a *vinca* alkaloid and a taxane, and administering between about 20 milligrams per day (mg/day) and about 1000 mg/day of a nonsteroidal selective glucocorticoid receptor modulator (SGRM), wherein the SGRM comprises a fused azadecalin structure having the formula:

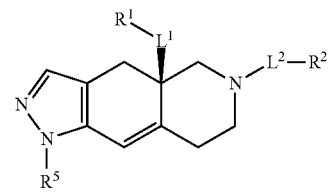

wherein $L^1$ and $L^2$ are members independently selected from a bond and unsubstituted alkylene;

$R^1$ is a member selected from unsubstituted alkyl, unsubstituted heteroalkyl, unsubstituted heterocycloalkyl, —$OR^{1A}$, $NR^{1C}R^{1D}$, —C(O) $NR^{1C}R^{1D}$, and —C(O) $OR^{1A}$, wherein $R^{1A}$ is a member selected from hydrogen, unsubstituted alkyl and unsubstituted heteroalkyl, $R^{1C}$ and $R^{1D}$ are members independently selected from unsubstituted alkyl and unsubstituted heteroalkyl, wherein $R^{1C}$ and $R^{1D}$ are optionally joined to form an unsubstituted ring with the nitrogen to which they are attached, wherein said ring optionally comprises an additional ring nitrogen;

$R^2$ has the formula:

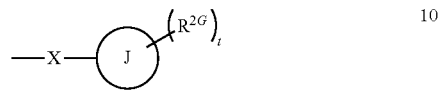

wherein $R^{2G}$ is a member selected from hydrogen, halogen, unsubstituted alkyl, unsubstituted heteroalkyl, unsubstituted cycloalkyl, unsubstituted heterocycloalkyl, —CN, and —CF$_3$;

J is phenyl;

t is an integer from 0 to 5;

X is —S(O$_2$)—; and $R^5$ is phenyl optionally substituted with 1-5 $R^{5A}$ groups, wherein $R^{5A}$ is a member selected from hydrogen, halogen, —OR$^{5A1}$, S(O$_2$)NR$^{5A2}$R$^{5A3}$, —CN, and unsubstituted alkyl, wherein $R^{5A1}$ is a member selected from hydrogen and unsubstituted alkyl, and $R^{5A2}$ and $R^{5A3}$ are members independently selected from hydrogen and unsubstituted alkyl, and salts thereof; or a heteroaryl-ketone fused azadecalin structure having the formula:

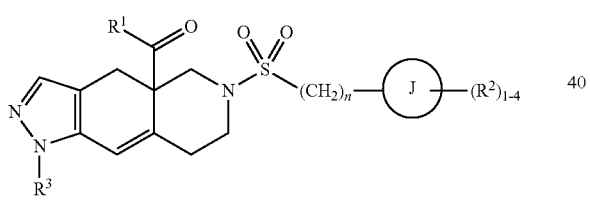

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;

each $R^{1a}$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, CN, N-oxide, C$_{3-8}$ cycloalkyl, and C$_{3-8}$ heterocycloalkyl;

ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S;

each $R^2$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, C$_{1-6}$ alkyl-C$_{1-6}$ alkoxy, CN, OH, NR$^{2a}$R$^{2b}$, C(O)R$^{2a}$, C(O)OR$^{2a}$, C(O)NR$^{2a}$R$^{2b}$, SR$^{2a}$, S(O)R$^{2a}$, S(O)$_2$R$^{2a}$, C$_{3-8}$ cycloalkyl, and C$_{3-8}$ heterocycloalkyl, wherein the heterocycloalkyl groups are optionally substituted with 1-4 $R^{2c}$ groups;

alternatively, two $R^2$ groups linked to the same carbon are combined to form an oxo group (=O);

alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups;

$R^{2a}$ and $R^{2b}$ are each independently selected from the group consisting of hydrogen and C$_{1-6}$ alkyl;

each $R^{2c}$ is independently selected from the group consisting of hydrogen, halogen, hydroxy, C$_{1-6}$ alkoxy, C$_{1-6}$ haloalkoxy, CN, and NR$^{2a}$R$^{2b}$;

each $R^{2d}$ is independently selected from the group consisting of hydrogen and C$_{1-6}$ alkyl, or two $R^{2d}$ groups attached to the same ring atom are combined to form (=O);

$R^3$ is selected from the group consisting of phenyl and pyridyl, each optionally substituted with 1-4 $R^{3a}$ groups;

each $R^{3a}$ is independently selected from the group consisting of hydrogen, halogen, and C$_{1-6}$ haloalkyl; and subscript n is an integer from 0 to 3;

and salts thereof; or an octahydro fused azadecalin structure having the formula:

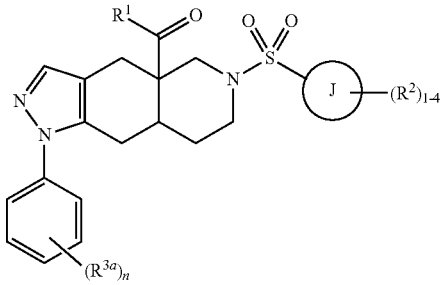

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;

each $R^{1a}$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, N-oxide, and C$_{3-8}$ cycloalkyl;

ring J is selected from the group consisting of an aryl ring and a heteroaryl ring having from 5 to 6 ring members and from 1 to 4 heteroatoms each independently selected from the group consisting of N, O and S;

each $R^2$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, C$_{1-6}$ alkyl-C$_{1-6}$ alkoxy, CN, OH, NR$^{2a}$R$^{2b}$, C(O)R$^{2a}$, C(O)OR$^{2a}$, C(O)NR$^{2a}$R$^{2b}$, SR$^{2a}$, S(O)R$^{2a}$, S(O)$_2$R$^{2a}$, C$_{3-8}$ cycloalkyl, and C$_{3-8}$ heterocycloalkyl having from 1 to 3 heteroatoms each independently selected from the group consisting of N, O and S;

alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups;

$R^{2a}$, $R^{2b}$ and $R^{2c}$ are each independently selected from the group consisting of hydrogen and $C_{1-6}$ alkyl;

each $R^{3a}$ is independently halogen; and subscript n is an integer from 0 to 3, and salts thereof, to reduce the tumor load of the pancreatic tumor.

2. The method of claim 1, wherein the non-ACTH-secreting pancreatic tumor is an exocrine pancreatic tumor.

3. The method of claim 1, wherein the antimicrotubule agent is a *vinca* alkaloid selected from the group consisting of vinorelbine, vincristine, vindesine, vinblastine, vincaleukoblastine, and combinations thereof.

4. The method of claim 1, wherein the antimicrotubule agent is a taxane selected from the group consisting of docetaxel, paclitaxel, nanoparticle albumin-bound paclitaxel (nab-paclitaxel), docosahexaenoic acid bound-paclitaxel (DHA-paclitaxel), polyglutamate bound-paclitaxel (PG-paclitaxel), ANG105 (Angiopep-2 bound to three molecules of paclitaxel), paclitaxel-EC-1 (paclitaxel bound to the erbB2-recognizing peptide EC-1), glucose-conjugated paclitaxel, and combinations thereof.

5. The method of claim 1, wherein the antimicrotubule agent is selected from the group consisting of nab-paclitaxel, paclitaxel, docetaxel, vinorelbine, vincristine, and vinblastine.

6. The method of claim 1, wherein the antimicrotubule agent is a taxane selected from docetaxel, paclitaxel, and nab-paclitaxel.

7. The method of claim 1, wherein the nonsteroidal selective glucocorticoid receptor modulator is a compound comprising a fused azadecalin structure having the following formula:

wherein $L^1$ and $L^2$ are members independently selected from a bond and unsubstituted alkylene;

$R^1$ is a member selected from unsubstituted alkyl, unsubstituted heteroalkyl, unsubstituted heterocycloalkyl, —$OR^{1A}$, $NR^{1C}R^{1D}$, —C(O) $NR^{1C}R^{1D}$, and —C(O) $OR^{1A}$, wherein $R^{1A}$ is a member selected from hydrogen, unsubstituted alkyl and unsubstituted heteroalkyl, $R^{1C}$ and $R^{1D}$ are members independently selected from unsubstituted alkyl and unsubstituted heteroalkyl, wherein $R^{1C}$ and $R^{1D}$ are optionally joined to form an unsubstituted ring with the nitrogen to which they are attached, wherein said ring optionally comprises an additional ring nitrogen;

$R^2$ has the formula:

wherein $R^{2G}$ is a member selected from hydrogen, halogen, unsubstituted alkyl, unsubstituted heteroalkyl, unsubstituted cycloalkyl, unsubstituted heterocycloalkyl, —CN, and —$CF_3$;

J is phenyl;

t is an integer from 0 to 5;

X is —$S(O_2)$—; and $R^5$ is phenyl optionally substituted with 1-5 $R^{5A}$ groups, wherein $R^{5A}$ is a member selected from hydrogen, halogen, —$OR^{5A1}$, $S(O_2)NR^{5A2}R^{5A3}$, —CN, and unsubstituted alkyl, wherein $R^{5A1}$ is a member selected from hydrogen and unsubstituted alkyl, and $R^{5A2}$ and $R^{5A3}$ are members independently selected from hydrogen and unsubstituted alkyl, and salts thereof.

8. The method of claim 7, wherein the nonsteroidal selective glucocorticoid receptor modulator comprising a fused azadecalin structure is:

9. The method of claim 1, wherein the nonsteroidal selective glucocorticoid receptor modulator is a compound comprising a heteroaryl ketone fused azadecalin structure having the formula:

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;

each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, CN, N-oxide, $C_{3-8}$ cycloalkyl, and $C_{3-8}$ heterocycloalkyl;

ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S;

each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups;

alternatively, two $R^2$ groups linked to the same carbon are combined to form an oxo group (=O);

alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups;

$R^{2a}$ and $R^{2b}$ are each independently selected from the group consisting of hydrogen and $C_{1-6}$ alkyl;

each $R^{2c}$ is independently selected from the group consisting of hydrogen, halogen, hydroxy, $C_{1-6}$ alkoxy, $C_{1-6}$ haloalkoxy, CN, and $NR^{2a}R^{2b}$, each $R^{2d}$ is independently selected from the group consisting of hydrogen and $C_{1-6}$ alkyl, or two $R^{2d}$ groups attached to the same ring atom are combined to form (=O);

$R^3$ is selected from the group consisting of phenyl and pyridyl, each optionally substituted with 1-4 $R^{3a}$ groups;

each $R^{3a}$ is independently selected from the group consisting of hydrogen, halogen, and $C_{1-6}$ haloalkyl; and subscript n is an integer from 0 to 3;

and salts thereof.

10. The method of claim 1, wherein the nonsteroidal selective glucocorticoid receptor modulator is a compound comprising a heteroaryl ketone fused azadecalin having the formula:

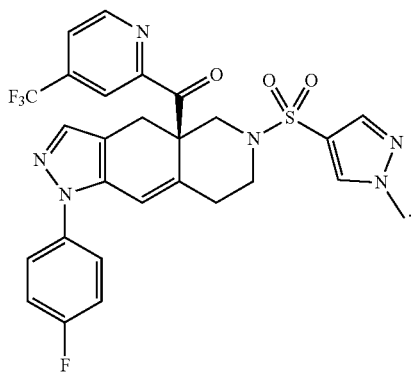 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

11. The method of claim 1, wherein the nonsteroidal selective glucocorticoid receptor modulator compound is a compound comprising an octahydro fused azadecalin structure having the formula:

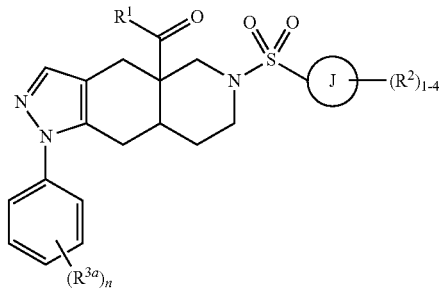

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;

each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl;

ring J is selected from the group consisting of an aryl ring and a heteroaryl ring having from 5 to 6 ring members and from 1 to 4 heteroatoms each independently selected from the group consisting of N, O and S;

each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl having from 1 to 3 heteroatoms each independently selected from the group consisting of N, O and S;

alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups;

$R^{2a}$, $R^{2b}$ and $R^{2c}$ are each independently selected from the group consisting of hydrogen and $C_{1-6}$ alkyl;

each $R^{3a}$ is independently halogen; and subscript n is an integer from 0 to 3, and salts thereof.

12. The method of claim 1, wherein the nonsteroidal selective glucocorticoid receptor modulator is a compound comprising an octahydro fused azadecalin which has the following structure:

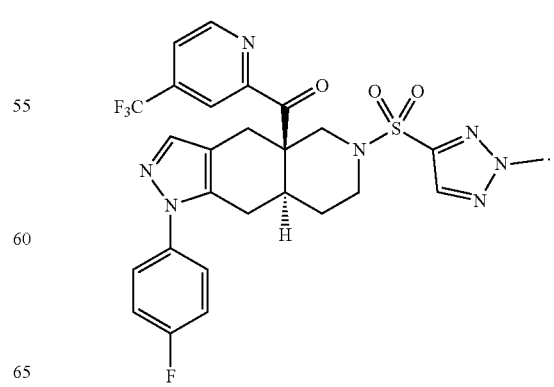

13. The method of claim 1, wherein the SGRM is administered intermittently.

14. The method of claim 7, wherein the SGRM is administered intermittently.

15. The method of claim 8, wherein the SGRM is administered intermittently.

16. The method of claim 9, wherein the SGRM is administered intermittently.

17. The method of claim 11, wherein the SGRM is administered intermittently.

18. The method of claim 12, wherein the SGRM is administered intermittently.

* * * * *